(12) United States Patent
Rameshwar et al.

(10) Patent No.: US 7,341,867 B2
(45) Date of Patent: Mar. 11, 2008

(54) HUMAN PREPROTACHYKININ GENE PROMOTER

(75) Inventors: Pranela Rameshwar, Maplewood, NJ (US); Pedro Gascon, Barcelona (ES)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 562 days.

(21) Appl. No.: 10/628,066

(22) Filed: Jul. 25, 2003

(65) Prior Publication Data

US 2004/0086919 A1    May 6, 2004

Related U.S. Application Data

(63) Continuation of application No. 09/747,429, filed on Dec. 23, 2000, now abandoned.

(60) Provisional application No. 60/171,970, filed on Dec. 23, 1999.

(51) Int. Cl.
*C12N 15/63* (2006.01)

(52) U.S. Cl. .................... 435/320.1; 536/24.1; 435/325

(58) Field of Classification Search ...................... None
See application file for complete search history.

(56) References Cited

FOREIGN PATENT DOCUMENTS

WO    WO 87/07643 A1    12/1987

OTHER PUBLICATIONS

Bost, K.L. and Pascual, D.W., Substance P: a late-acting B lymphocyte differentiation cofactor. Am. J. Physiol. 262:C537-545 (1992).

Bunn, P.A. et al., Effects of Neuropeptide Analogues on Calcium Flux and Proliferation in Lung Cancer Cell Lines. Cancer Research 54:3602-3610 (1994).

Cremins, J.D. et al., Characterization of Substance P-Like Immunoreactivity and Tachykinin-Encoding mRNAs in Rat Medullary Throid Carcinoma Cell Lines. Journal of Neurochemistry 58:817-824 (1992).

Everard, M.J. et al., In vitro effects of substance P analogue ($D-Arg^1$, $D-Phe^5$, $D-Trp^{7,9}$, $Leu^{11}$) substance P on human tumour and normal cell growth. British Journal of Cancer 65:388-92 (1992).

GENEMBL accession No. S69719.

Gilchrist et al (DNA Cell Biol 10, 743-749 abstract only).

Hennig, I.M. et al., Substance-P Receptors in Human Primary Neoplasms: Tumoral and Vascular Localization. Int. J. Cancer 61:786-792 (1995).

Jones, D.A. et al., Processing [$D-Arg^1$, $D-Phe^5$, $D-Trp^{7,9}$, $Leu^{11}$] Substance P in Xeograft Bearing *Nu/Nu* Mice. Peptides 18:1073-1077 (1997).

McGregor, G.P. et al., Preprotachykinin-A Gene Expression Occurs Transiently in the Developing Rat Endocrine Pancreas and Can Be Regulated in RINm5F Cells. Endocrinology 136:2538-2546 (1995).

(Continued)

*Primary Examiner*—Misook Yu
(74) *Attorney, Agent, or Firm*—Licata & Tyrrell PC

(57) ABSTRACT

Compositions and methods are provided for identifying novel therapeutic agents for the treatment of breast cancer, bone marrow metastasis, pain, arthritis, aggressive behavior, depression, and certain hematopoietic disorders. Disclosed are promoters and 3' regulatory regions of genes whose expression differs in malignant cells as compared with non-malignant cells. These include PPT-I, NK-2 and SP-R.

3 Claims, 8 Drawing Sheets

OTHER PUBLICATIONS

Moore, R.N. et al., Substance P Augmentation of CSF-1-Stimulated in vitro Myelopoiesis. The Journal of Immunology 141:2699-2703 (1988).

Rameshwar, Pranela et al., *Neural Regulation of Hematopoiesis by the Tachykinins, Implications for a "Fine Tuned" Hematopoietic Regulation*, Molecular Biology of Hematopoiesis 5, pp. 463-470 (1996).

Rameshwar, Pranela et al., *Substance P (SP) Mediates Production of Stem Cell Factor and Interleukin-1 in Bone Marrow Stroma: Potential Autoregulatory Role for These Cytokines in SP Receptor Expression and Induction*, Blood, vol. 86, No. 2 Jun. 15, 1995: pp. 482-490.

Rameshwar, Pranela et al., *Hematopoietic Regulation Mediated by Intearctions Among the Neurokinins and Cytokines*, Leukemia and Lymphoma, vol. 28, pp. 1-10.

Ramshwar, Pranela et al., *Release and Interleukin-1 and Interleukin-6 From Human Monocytes by Antihymocyte Globulin: Requirement for De Novo Synthesis*, Blood, vol. 80 Nov. 15, 1992: pp. 2531-2538.

Rameshwar, Pranela et al., *Molecule of the Month, Substance P.: A Regulatory Neuropeptide for Hematopoiesis and Immune Functions[1]*, Clinical Immunology and Immunopathology, vol. 85, No. 2, November, pp. 129-133, 1997, Article No. II974446.

Rameshwar, Pranela et al., *Induction of Negative Hematopoietic Regulators by Neurokinin-A in Bone Marrow Stroma*, Blood, vol. 88, No. 1 Jul. 1, 1996: pp. 98-106.

Rameshwar, Pranela et al., *Receptor Induction Regulates the Synergistic Effects of Substance P with IL-1 and Platelet-Derived Growth Factor on the Proliferation of Bone Marrow Fibroblasts[1]*, The Journal of Immunology, 1997, 158: 3417-3424.

Rameshwar, Pranela et al., *In Vitro Stimulatory Effect of Substance P on Hematopoiesis*, Blood, vol. 81 Jan. 15, 1993: pp. 391-398.

Reeve, J.G. and Bleehen, N.M., [D-Arg$^1$, D-Phe$^5$, D-Trp$^{7,9}$, Leu$^{11}$] Substance P Induces Apoptosis in Lung Cancer Cell Lines in vitro. Biochemical and Phophysical Research Communications 199: 1313-1319 (1994).

Singh, Deeppreet et al., *Increased expressions of preprotachykinin-1 and neurokinin receptors in human breast cancer cells: Implications for bone marrow metastasis*, PNAs, Jan. 4, 2000, vol. 97, No. 1, pp. 388-393.

Theodorsson-Norheim, E. et al., Isolation and characterization of neurokinin A, neurokinin A(3-10) and neurokinin A (4-10) from a neutral water extract of a metastatic ileal carcinoid tumour. Eur. J. Biochem 166:693-695 (1987).

Webber, R.H. et al., Bone marrow response to stimulation of the sympathetic trunks in rats. Acta. anat. 77:9297 (1970).

Winkler, A. et al., Expression and characterization of the substance P ($NK_1$) receptor in the rat pituitary and AtT20 mouse pituitary tumor cells. European Journal of Pharmacology 291: 51-55 (1995).

GENEMBL accession No. S69719, May 7, 1993.

Gilchrist et al (DNA Cell Biol 10, 743-749 abstract only), Dec. 1999.

Rameshwar, Pranela et al., *Hematopoietic Regulation Mediated by Intearctions Among the Neurokinins and Cytokines*, Leukemia and Lymphoma, vol. 28, pp. 1-10, Dec. 1997.

```
                              CG ACGGCCCGGC TGGTAAATTC CCCTTTCTCC
-690 AAAATGTAAA ATAAATCTGC TTCCATCTTC TAAAATACTA TGGGACTAAA
-640 CATCCTTTTG TTATGCTAAG GAAAAGCCAG TATTCGCGTT GATTTAGAAG
-590 AGGGATGTTC TGGTTATAGA ACGATGCTGT GTCTCAGAAA CACTTAAATA
-540 CTATTAAGCT AGAAATAGAA GGGAAAATAA TGCTTCCCCG CATCTCCCCT
-490 CAAGTGTAGT CCTCTTTTTT TAGCCTGATT TCCGACGAAA TGTCTGAATG
-440 CCTACAGTTA TTTGGCCATC CTGAAAAGTG CAACTTATCC TGACGTCTCG
                                                       CRE
-390 AGGGACGGAA AAGTTACCGA AGTCCAAGGA ATGAGTCACT TTGCTCAAAT
-340 TTGATGAGTA ATATCAGGTG TCATGAAACC CAGTTTCGAA GGAGAGGGGA
-290 GGGGGCGTCA GATCTGCAGA CGGAAGCAGG CCGCTCCGGA TTGGATGGCG
-240 AGACCTCGAT TTTCCTAAAA TTGCGTCATT TAGAACCCAA TTGGGTCCAG
                                    CRE-like
-190 ATGTTATGGG CATCGACGAG TTACCGTCTC GGAAACTCTC AATCACGCAA
-140 GCGAAAGGAG AGGAGGCGGC TAATTAAATA TTGAGCAGAA AGTCGCGTGG
 -90 GGAGAATGTC ACGTGGGTCT GGAGGCTCAA GGAGGCTGGG ATAAATACCG
 -40 CAAGGCACTG AGCAGGCGAA AGAGCGCGCT CGGACCTCCT
  +1 TTCCCGGCGG CAGCTACCGA GAGTGCGGAG CGACCAGCGT GCGCTCGGAG
     Exon 1
 +51 AACCAGAGAA CTCAGCACCC CGCGGGACTG TCCGTCGCAG TAAGTGCCCG
                                                      Intron 1
+101 CGCGGTGCTG GCCGCGGCTG CCCGGGTCAT CCCACCCCGC ATCTGTCCGA
+151 GGTGGCCGCG CTGGGGCGC CGCTGCGGCG AGGGACAGTG GGGAGACTGG
+201 CTTCCCAAAC GCCAACGCCC CTCTTTGTCT TCCACCTGCA GAGTTTCCTG
+251 GTTTGAAGGT GTGGGTTGGT GGGTTAGGGG GCTGGGGGAG CTGGGATTCA
+301 GGGAGAAGAG GGTTGGAGAA TCTTTGGGAC GCGATTCTCT CGCCTAACCG
+351 GTACAGGTGA GACTTCAGTC CTTATGTTTT TGATCTTGGT TCATCCGTTG
+401 TGGGGCAGAA AATTCTGTTG CTTAACTCT TGGATAACCA CCCCTAATAG
+451 ATACATTATT TCTCTCTTTG GTGTCTTCTC CTCCTACCCC TTCCCAGAAA
                                                       Exon 2
+501 TCCGAC
```

FIG. 2

FIG. 4A
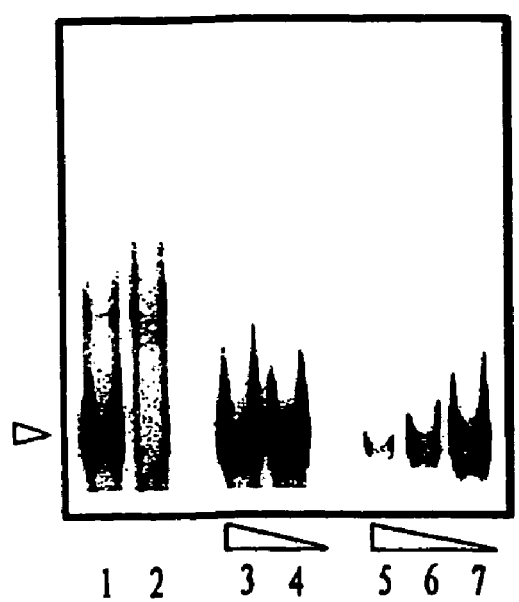
FIG. 4C
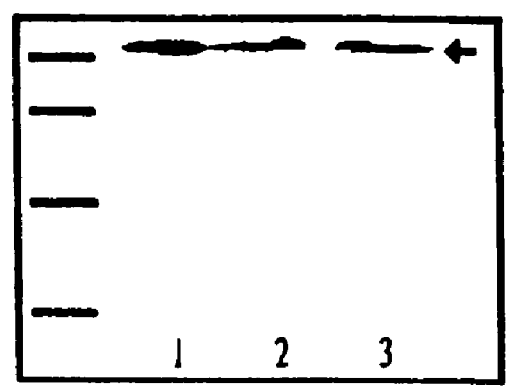
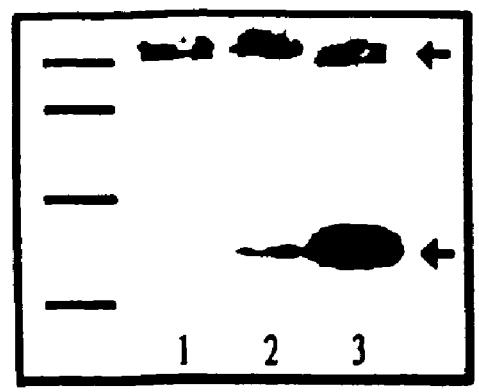
FIG. 4B
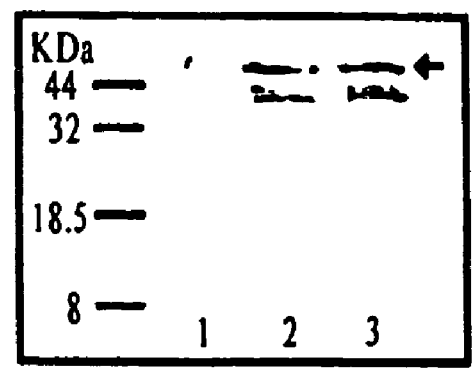
FIG. 4D

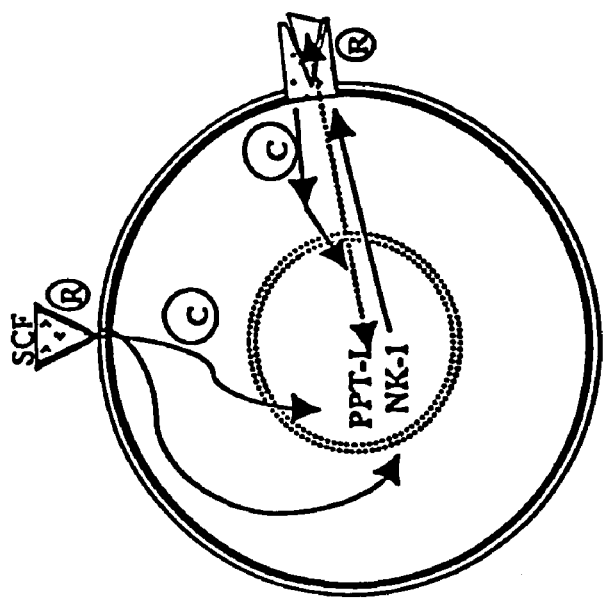
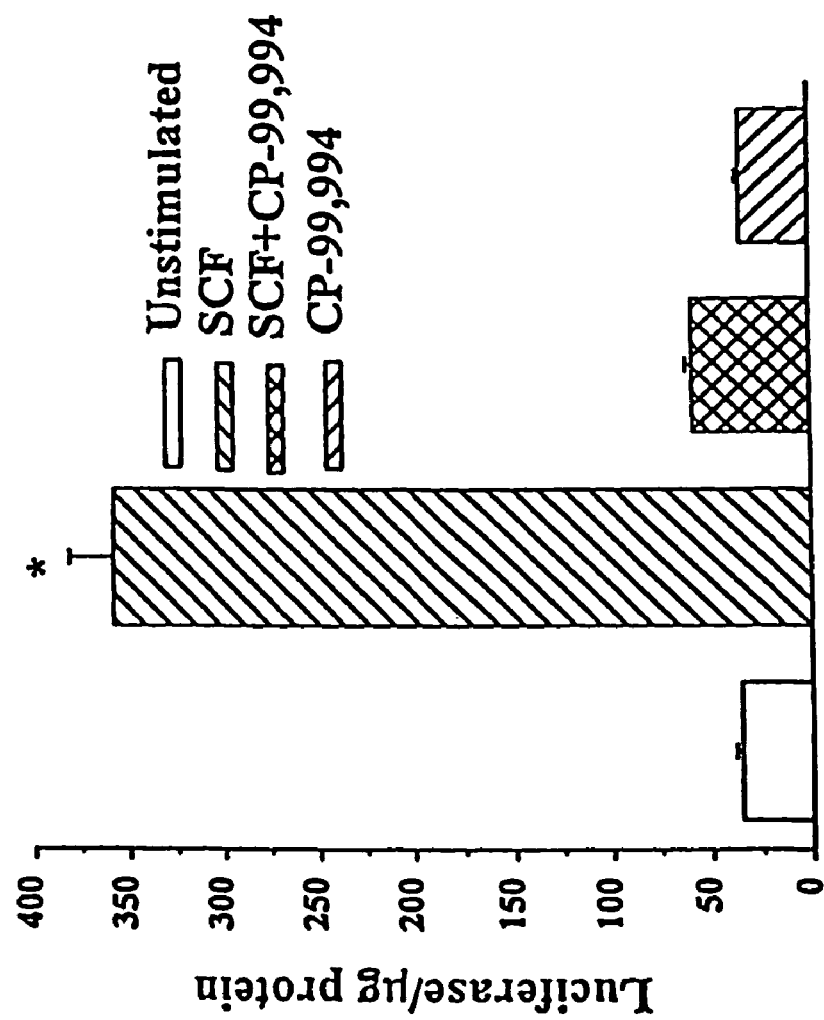
FIG. 7B
FIG. 7A

HUMAN PREPROTACHYKININ GENE PROMOTER

This application is a continuation of U.S. application Ser. No. 09/747,429, filed Dec. 23, 2000, now abandoned, which claims the benefit of U.S. Provisional Application No. 60/171,970, filed Dec. 23, 1999. Both of these applications are incorporated by reference herein in their entirety.

Pursuant to 35 U.S.C. § 202 (c) it is acknowledged that the U.S. Government has certain rights in the invention described herein, which was made in part with funds from the National Institutes of Health, Grant Numbers HL57675 and HL54973.

FIELD OF THE INVENTION

This invention relates to the fields of molecular biology, drug discovery and neoplastic transformation. More specifically, nucleic acid molecules encoding a preprotachykinin (PPT) gene promoter or 3' mRNA operably linked to a nucleic acid encoding a reporter molecule are provided for use in methods for identifying beneficial therapeutic reagents which influence expression levels and biochemical functions of this protein. The compositions of the invention may be used to advantage in the discovery of therapeutic agents for the treatment of cancer and other hematologic disorders.

BACKGROUND OF THE INVENTION

The immune-hematopoietic-neural axis encompasses the neuroendocrine system. These two systems cooperate via biochemical cross-talk. A particular cytokine or neuropeptide can be produced in cells of both neural and peripheral tissue, the latter including lymphoid organs and bone marrow, among others. Soluble factors mediate this bidirectional communication between the nervous and immune/hematopoietic systems. Due to this crosswalk, changes in one system often influence functional changes in the other. In fact, studies show that the onset of hematopoiesis is correlated with complete innervation of the bone matter.

Stress, either physical, chemical or psychological, induces soluble brain derived factors and has been implicated in altered immune functions. Stress has also been associated with the incidence, relapse and prognosis of cancer. Specifically, stress-induced neurohormones have been implicated in the development of breast cancer. Biological homeostasis is achieved by the complex interacting network of all these soluble factors. The interactions of neurohormones and neurotransmitters are not mutually exclusive of the interactions exerted by cytokines and neurotrophic factors. Dysregulated and inappropriate expression of factors, such as neuroendocrine-derived peptides, disrupts homeostasis. Ultimately, tumors may develop as a result of disrupted homeostasis. An example of this type of dysregulation is the constitutive expression of neurokinins observed in some tumors.

The Preprotachykinin-I (PPT-I) gene encodes a family of peptides that interact with a network of soluble factors in neural and non-neural tissues to exert biological pleiotropism, such as neurotransmission, immune modulation and hematopoiesis (Rameshwar, P. 1997, *Clin. Immunol. Immunopath*, 85:129; Maggi, C. A. 1996, *Pharmacol. Res*. 33:161; Merril, J. E. et al. 1995, *FASEB J*., 9:611). The role of PPT-I in hematopoiesis and angiogenesis, and its over expression in breast and other cancers that metastasize to the bone marrow, suggests that PPT-I has a central role in: bone marrow metastasis (Singh, D. et al. 2000, *Proc. Nat'l. Acad. Sci U.S.A*. 97:388; Hennig, I. M. et al. 1995, *Int. J. Cancer* 61:786; Jones, D. A. et al. 1997, *Peptides* 18:1073). The evolutionarily conserved sequence of PPT-I peptides underscores the importance of the pleiotropism that these peptides demonstrate in interactive biological functions (Moore, T. C. et al. 1990 *Immunopharmacol* 20:207). The ability to manipulate and understand the regulation of PPT-I may help to facilitate modulation of the molecular mechanisms mediated by this gene that underlie organ specific functions and provide new insights into human pathology such as tumor-genesis, hematological diseases, nerve damage and other brain-associated functions and/or behavior.

Neurokinins are a family of neurotransmitters derived from expression of the preprotachykinin-I (PPT-I) gene. This gene is also expressed in a variety of non-neuronal cells. The PPTI gene is alternatively spliced into one of four transcripts, α, β, γ, and δ PPT-I. Each transcript can produce substance P (SP). The γ and δ PPT-I transcripts produce neurokinin-A (NK-A). Various N-terminally extended forms of NK- are also expressed from the PPT-I gene.

Regulated expression of SP and NKA and other biological mediators act in concert to maintain homeostasis. Overproduction of SP and NKA can contribute to neoangiogenesis, facilitating the growth of metastatic tumors. While SP exerts angiogenic properties directly, NK-A has the potential to exert indirect angiogenic function through TGF-β production. The elucidation of this relationship is desirable for developing therapeutic agents for the treatment of cancer. In particular, agents which regulate the expression of PPT-I may be efficacious in the treatment of cancers and other hematopoietic disorders.

In the bone marrow, the two major PPT-I peptides, through their natural neurokinin receptors, NK-1 and NK-2, exert opposing influences, inhibitory and stimulatory, on hematopoiesis at the level of the mature and immature progenitors (Rameshwar, P. et al. 1997, *Leuk. Lymphoma* 28:1). Therefore, hematopoietic stimulation by one of the major PPT-I peptides may be clinically important in hematologic deficiencies such as in the development of neutropenia and also other inflammatory responses (Cao, T. et al. 2000, *J. Immunol* 164:5424). The inhibitory effect could be important in protection of the lymphohematopoietic stem cells in the bone marrow, where maintaining cell quiescence is often important. Furthermore, PPT-I is involved in the cellular and molecular connection among the immune, neuroendocrine and hematopoietic systems (Rameshwar, P. 1997, supra.). Thus, the regulation of PPT-I has relevance to bone marrow-associated biology, including the rapidly evolving fields of transplantation and gene therapy and also, inflammatory processes.

Bone marrow fibrosis is a pathological secondary reaction which occurs in certain myeloproliferative disorders. Whereas the mechanisms that lead to bone marrow fibrosis are poorly understood, it has been hypothesized that soluble factors such as platelet derived growth factor (PDGF), transforming growth factor β (TGF-β) and epidermal growth factor (EGF) act to induce deposits of extracellular matrix proteins in the bone marrow. TGFβ stimulates synthesis of collagen and fibronectin in fibroblasts and also augments the proliferation of human bone marrow fibroblasts by EGF and PDGF. The NK-1 receptor shares homology with regions of fibronectin. Preliminary studies show that substance P (SP), the preferred ligand for NK-1, binds to fibronectin in the sera of patients with various categories of bone marrow fibrosis. SP is a fibrogenic factor and a stimulator of macrophages. As fibroblasts and macrophages are implicated in the pathophysiology of bone marrow fibrosis, SP is transported to the bone marrow and other organs via binding to fibronectin. Accordingly, PPT-I (the gene from which SP is derived) provides a suitable target for treatment of patients with bone marrow fibrosis. Since bone marrow fibrosis is secondary to myeloproliferative disorders, PPT-I genes, their encoded peptides and their receptors, and/or pathways associated with the products of these genes can also serve as targets to identify beneficial therapeutic reagents for treating patients with such disorders.

SUMMARY OF THE INVENTION

In one embodiment of the invention, an isolated polynucleotide comprising a PPT-I promoter region is provided. In one embodiment, this region occupies a segment of a human PPT-I gene between about 722 bases upstream from a transcription initiation site of the gene, and encompassing the transcription initiation site, as shown in FIG. 2. Preferably, the PPT-I promoter is isolated from a gene whose coding region hybridizes under moderate conditions with a coding region of a PPT-I gene, such as that shown in SEQ ID NO:15. Most preferably, this promoter region comprises SEQ ID NO:1. The PPT-I promoter sequence of the invention contains a plurality of CRE regulatory sequence elements, and other transcription factor responsive elements. Expression vectors comprising the PPT-I promoter sequence operably linked to a heterologous nucleic acid molecule are also within the scope of the present invention. In a preferred embodiment of the invention, the heterologous nucleic acid molecule encodes a reporter gene. Reporter genes suitable for this purpose include, without limitation, β-galactosidase, chloramphenicol acetyltransferase, luciferase, secreted alkaline phosphatase and green fluorescent protein.

In another embodiment of the present invention, an isolated polynucleotide comprising a PPT-I gene 3' end mRNA is provided. Preferably, the PPT-I 3' region is isolated from a gene whose coding region hybridizes under moderate conditions with a coding region of a PPT-I gene, such as that shown in SEQ ID NO:15. In a highly preferred embodiment, the sequence of this polynucleotide comprises SEQ ID NO:4.

The present invention also features an isolated polynucleotide comprising a the upstream region of exon 1 of a gene encoding the neurokinin receptor, NK-2. Preferably, this promoter is isolated from a gene having a coding region defined by the exons set forth in SEQ ID NO:2. More preferably, this upstream region is that shown in SEQ ID NO:2. The upstream NK-2 sequence of the invention contains a plurality of CRE regulatory sequence elements, and other transcription factor responsive elements. Expression vectors comprising the NK-2 upstream sequence operably linked to a heterologous nucleic acid molecule are also within the scope of the present invention. In a preferred embodiment of the invention, the heterologous nucleic acid molecule encodes a reporter gene. Reporter genes suitable for this purpose include, without limitation, β-galactodosidase, chloramphenicol acetyltransferase, luciferase, secreted alkaline phosphatase and green fluorescent protein.

Also included in the present invention is an isolated polynucleotide comprising a promoter and gene for the SP receptor (SP-R). Preferably, this promoter is isolated from a gene having a coding region defined by the exons as set forth in SEQ ID NO:3. More preferably, this upstream region is that shown in SEQ ID NO:3. The upstream SP-R sequence of the invention contains a plurality of CRE regulatory sequence elements, and other transcription factor responsive elements. Expression vectors comprising the SP-R promoter operably linked to a heterologous nucleic acid molecule are also within the scope of the present invention. In a preferred embodiment of the invention, the heterologous nucleic acid molecule encodes a reporter gene. Reporter genes suitable for this purpose include, without limitation, β-galactosidase, chloramphenicol acetyltransferase, luciferase, secreted alkaline phosphatase and green fluorescent protein.

In yet further aspect of the invention, an isolated host cell transformed with the expression vectors described above is provided. Host cells contemplated for use in this aspect of the invention include procaryotic, eucaryotic, fungal, plant, mammalian and insect cells.

In a further aspect of the invention a process for producing a host cell containing a heterologous gene operably linked to the above mentioned sequences is provided. The process comprises i) transfecting a cell with an expression vector comprising a heterologous gene operably linked to the sequence; ii) simultaneously transfecting the cell with a selectable marker gene which confers resistance to a selection agent; and iii) selecting and isolating transformed host cells on the basis of resistance to the selection agent, the host cell also containing a heterologous gene operably linked to the inventive sequence. In this embodiment of the invention, the selectable marker gene may or may not be on the same expression construct as the inventive sequence/reporter gene construct.

Methods utilizing the expression constructs and host cells containing the same for identifying agents which affect the promoter activity of the PPT-I, or the NK-2 gene are also provided in the present invention. Similarly, methods utilizing the expression constructs and host cells containing the same for identifying agents which affect activity of the SP receptor (SP-R) gene are provided in the present invention. Transformed host cells are contacted with an agent which inhibits or stimulates promoter activity. Influence of the test agent on promoter function is determined based on levels of expression of the reporter gene relative to the appropriate negative controls.

Also included in the present invention are methods for screening the PPT-I promoter, NK-2 upstream sequence or SP-R gene for mutations associated with pathological conditions.

Preferably, the polynucleotides of the invention comprise a sequence selected from the following group: SEQ ID NO:1; an allelic variant of SEQ ID NO:1; a sequence hybridizing with SEQ ID NO:1 or its complement under moderate hybridization and washing conditions; SEQ ID NO:2; an allelic variant of SEQ ID NO:2; a sequence hybridizing with SEQ ID NO:2 or its complement under moderate hybridization and washing conditions; SEQ ID NO:3; an allelic variant of SEQ ID NO:3: a sequence hybridizing with SEQ ID NO:3 or its complement under moderate hybridization and washing conditions; SEQ ID NO:4; and an allelic variant of SEQ ID NO:4; a sequence hybridizing with SEQ ID NO:4 or its complement under moderate hybridization and washing conditions.

Another aspect of the invention features a recombinant DNA molecule comprising a vector having an insert that includes part or all of a PPT-I promoter or 3' sequence, NK-2 upstream sequence, or SP-R promoter and/or gene and cells transformed with any of the above-mentioned recombinant DNA molecule. Preferably, the cells are human cells. Most preferably, the cells are from breast tissue cells, breast cancer cells, fibroblast cells, or epithelial cells.

The invention also features an isolated polypeptide produced by expression of the polynucleotides described above.

Antibodies immunologically specific for the protein, or one or more epitopes thereof, are also provided.

In another aspect, the invention relates to methods for using such polypeptides and polynucleotides, including the treatment of breast cancer, bone marrow metastasis, pain, asthma, arthritis, aggressive behavior, and depression, where one or more of PPT-I peptides, NK-2 or SP-R is known to play a role. In still another aspect, the invention relates to methods to identify agonists and antagonists using the materials provided by the invention, and treating diseases or conditions associated with PPT-I, NK-2 or SP-R imbalance with the identified compounds.

BRIEF DESCRIPTION OF THE DRAWINGS

FIG. 2 depicts the sequence of the longest fragment cloned upstream of Exon 2, PPT-I (SEQ ID NO:14, which is a variant of SEQ ID NO:1). Nucleotides are numbered relative to exon 1. The TATA box is in bold. There are 722 nt upstream of Exon 1. Underlined sequences show consensus sequences for CRE, the 5' ends of Exon 1 (+1/+89) and Intron 1 (+90/+498). Consensus sequences for NF-κB, shown by double underline, are found towards the end of the 5' region and within Exon 1. GenBank Accession Number AF252261.

FIG. 4. FIG. 4A is a representative gel shift of four different experiments showed that CRE and CRE-like can bind ICERIIγ using wild type or mutant oligonucleotide probes. Lanes 1: wild type; 2: mutant; 3 and 4: 200 and 50 ng mutant cold competitor respectively; 5, 6 and 7: 200, 100 and 50 ng wild type cold competitor respectively. (▷) protein-DNA interactions. FIGS. 4B, 4C and 4D are representative western blots of three different experiments were determined for CRE-binding proteins in bone marrow stroma with an antibody that reacts with CREM (B: top arrow) and ICERIIγ (B: lower arrow), anti CREB (C) or anti-phospho CRE-activators (D: top lanes, CREM and CREB; bottom lanes: ATF-1). Extreme left lanes: molecular weight marker. Lanes 1: unstimulated stroma; 2: FK-2h; 4: FK-5h.

FIG. 5 shows representative data of six different experiments that were performed with bone marrow stroma, transiently transfected with pGL3 basic-Upstream/N0 that contained wild type or mutant CRE and/or mutant CRE-like (Table 1). Cells were co-transfected with 200 ng/µl of pSV that expressed: 1. PKA and CREMτ, 2. PKA or, 3. PKA, CREMτ and ICERIIγ.

FIG. 8B: *p<0.05 vs. CREMτ, **p<0.05 vs. Upstream/N0 or Upstream/N0, CREMτ. Each experimental point is the mean (±SD) of duplicate transfections with 7 bone marrow donors.

FIG. 7 shows the effects of NK-1R antagonist on the activation of PPT-I promoter by SCF. FIG. 7A: bone marrow stromal cells, transfected with pGL3-Upstream/N0 were stimulated with 8 ng/ml SCF or 2.5 ng/ml IL-1α for 36 h. During the middle of the incubation period, culture media with cytokines were replaced. After this, cells were washed and then incubated within 0.1 nM CP-99,994. After 8 h, luciferase activity was determined in cell lysates as described for FIG. 6. FIG. 7B: Model to explain indirect stimulation of PPT-I by a representative cytokine. SCF-receptor interaction leads to induction of PPT-I and NK-1. The peptides derived from PPT-I transcription are released and interact with the G-protein coupled NK-1 on the cell membrane. PPT-I-peptide-NK-1 interaction results in activation of cAMP pathway, which activates putative kinase(s), thus activation of the two CRE regions within PPT-I promoter. *p<0.01 vs. unstimulated or SCF+CP-99,994. © cAMP pathway; ® Receptor.

DETAILED DESCRIPTION OF THE INVENTION

Figure 1:
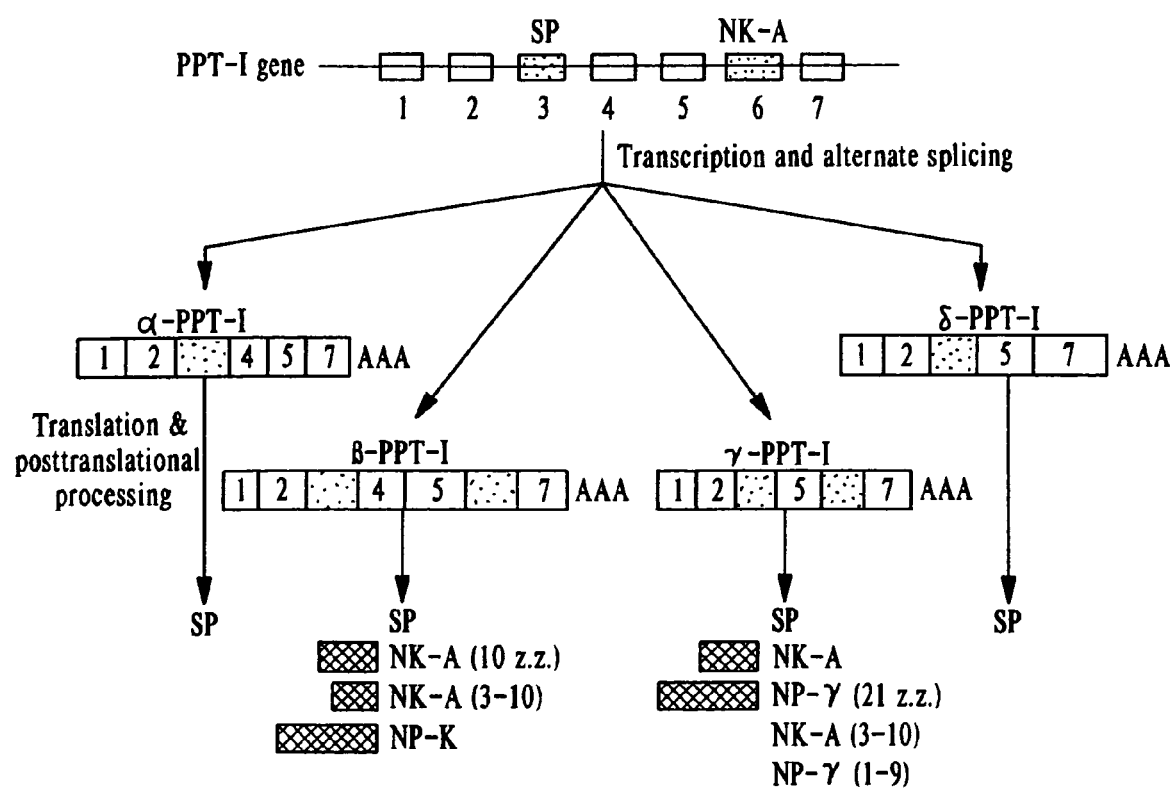
FIG. 1 is a schematic diagram of the PPT gene showing the alternative splicing of the PPT mRNA transcript. Also depicted is the promoter region of the PPT gene.

The following definitions are provided to facilitate an understanding of the present invention.

"PPT-I gene" or "PPT-I" refers to a polynucleotide as defined above in accordance with the present invention, which encodes PPT-I peptides.

"PPT-I" or "PPT-I peptides" refer generally to peptides or polypeptides encoded by PPT-I.

"PPT-I activity or PPT-I polypeptide activity" or "biological activity of the PPT-I or PPT-I polypeptide" refers to the metabolic or physiologic function of said PPT-I including similar activities or improved activities or these activities with decreased undesirable side-effects. Also included are antigenic and immunogenic activities of said PPT-I.

"NK-2" or "NK-2 gene" refers to a polynucleotide as defined above in accordance with the present invention, which encodes an NK-2 polypeptide.

"NK-2" refers generally to a polypeptide encoded by NK-2, which is described in detail herein above and throughout the specification. NK-2 is a neurokinin receptor, and is also sometimes referred to herein as "NK-2R", and the terms are meant to be used interchangeably.

"NK-2 activity or NK-2 polypeptide activity" or "biological activity of the NK-2 or NK-2 polypeptide" refers to the metabolic or physiologic function of said NK-2 including similar activities or improved activities or these activities with decreased undesirable side-effects. Also included are antigenic and immunogenic activities of said NK-2.

NK-1 is also a neurokinin receptor and its regulation in various cell types is discussed in detail herein. NK-1 is also sometimes referred to herein as "NK-1R", and the terms are meant to be used interchangeably.

"SP-R gene" refers to a polynucleotide which encodes an SP receptor polypeptide.

"SP-R" or "Substance P receptor" refers generally to a polypeptide encoded by SP-R, which is described in detail herein above and throughout the specification.

"SP-R activity or SP-R polypeptide activity" or "biological activity of the SP-R or SP-R polypeptide" refers to the metabolic or physiologic function of said SP-R including similar activities or improved activities or these activities with decreased undesirable side-effects. Also included are antigenic and immunogenic activities of said SP.

"Antibodies" as used herein includes polyclonal and monoclonal antibodies chimeric, single chain, and humanized antibodies, as well as Fab fragments, including the products of an Fab or other immunoglobulin expression library. With respect to antibodies, the term, "immunologically specific" refers to antibodies that bind to one or more epitopes of a protein of interest, but which do not substantially recognize and bind other molecules in a sample containing a mixed population of antigenic biological molecules.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide, Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626-646 and Rattan et al., "Protein Synthesis: Posttranslational Modifications and Aging", *Ann NY Acad Sci* (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

The term "substantially the same" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

"Identity" and "similarity" can be readily calculated by known methods. Nucleic acid sequences and amino acid sequences can be compared using computer programs that align the similar sequences of the nucleic or amino acids thus define the differences. In preferred methodologies, the BLAST programs (NCBI) and parameters used therein are employed, and the DNAstar system (Madison, Wis.) is used to align sequence fragments of genomic DNA sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

With respect to oligonucleotides, but not limited thereto, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate to the compound of interest (e.g. chromatographic methods, agarose or polyacrylamide gel electrophoresis, HPLC analysis, and the like).

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA". Such a nucleic acid construct may contain a coding sequence for a gene product of interest, along with a selectable marker gene and/or a reporter gene.

The term "selectable marker gene" refers to a gene encoding a product that, when expressed, confers a selectable phenotype such as antibiotic resistance on a transformed cell.

The term "reporter gene" refers to a gene that encodes a product which is detectable by standard methods, either directly or indirectly.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

As used herein, the term "test subject" or "patient" shall include both mammals and humans.

Neuropeptides have been observed in many tumors, including breast cancer. The preprotachykinin-I gene (PPT-I) encodes multiple neuropeptides that exert pleiotropic functions, including neurotransmission, immune/hematopoietic modulation, angiogenesis and mitogenesis. PPT-I is constitutively expressed in some tumors. In accordance with the present invention, a role for PPT-I and its receptors, NK-1 and NK-2, in breast cancer has been determined, using quantitative RT-PCR, ELISA and in situ hybridization. In breast cancer cell lines and malignant breast biopsies, increased expression of PPT-I, NK-1 and NK-2 genes was observed. In normal mammary epithelial cells and benign breast biopsies, NK-2 levels are elevated, while NK-1 and PPT-I peptides are not detected. Specific NK-1 and NK-2 antagonists inhibit breast cancer cell proliferation, suggesting autocrine and/or intercrine stimulation of breast cancer cells by PPT-I peptides. Unlike normal cells where NK-2 maintains cell quiescence, NK-2 mediates cell proliferation in breast cancer cells.

Further, it was discovered in the present invention that cytosolic extracts from malignant breast cancer cells enhance PPT-I translation, whereas extracts from normal mammary epithelial cells fail to enhance translation. These enhancing effects of malignant cell extracts on PPT-I appear to be protein specific, as a similar increase was observed for IL-6 translation, but no effect was detected for IL-1α (and SCF translation. These findings further implicate a role for PPT-I peptides and their receptors in the development of breast cancer. Considering that PPT-I peptides are hematopoietic modulators, these results provide insight into the events leading to early integration of breast cancer cells in the bone marrow, a preferred site of metastasis. The manipulation of molecular signaling transduced by PPT-I peptides and the mechanism that enhances translation of PPT-I mRNA enable development of innovative strategies for treating breast cancer and metastasis.

As described in greater detail herein, the inventors have cloned the genomic sequences upstream of the coding region of human PPT-I, and identified the area with promoter activity. Several modulators of PPT-I regulation activate the cAMP pathways. The inventors have discovered the consensus sequences for two cAMP response elements (CRE) in the promoter region of PPT-I, which are involved in the regulation of PPT-I expression. Several transcription factors can bind as dimers to CRE: CREM (CRE modulator), CREB (CRE binding proteins) and activator transcription factor-1, ATF-1 (Molina, C. A. 1997. J. L. Tilly, et al., Verlag, NY. p. 182; Sassone-Corsi, P. 1995., Annu. Rev. Cell. Dev. Biol 11:355). CRE-interacting proteins are primarily constitutive, and their activation requires cAMP-dependent PKA (Molina, C. A. supra). A second internal promoter in the CREM gene can be induced by cAMP to produce a repressor, ICER (inducible cAMP early repressor), which is a negative regulator of cAMP-induced transcription (Molina, C. A. supra; Sassone-Corsi, P., supra). In accordance with the present invention, areas of mutations in the promoter of PPT-I gene associated with breast cancer, breast cancer metastasis and certain hematopoietic disorders have been identified.

In organs where PPT-I is important to maintain steady-state functions, cytokines are important for regulating its expression (Rameshwar, P. 1997, supra). Therefore, the present invention utilizes representative cytokines to determine the role of CRE and CRE-like sequences in cytokine-mediated PPT-I regulation. Cytokines are believed to activate the cAMP pathway through direct and/or indirect mechanisms (Masuda, E. S. et al 1993. The Immunologist 1/6:198). Indirect stimulation could occur through the induction of other soluble factors that can stimulate the cells through autocrine and/or paracrine mechanisms. The inventors have shown that IL-1α and stem cell factor (SCF) require the two CREs for optimal promoter activity. The use of a specific NK-1 antagonist demonstrates that SCF induces PPT-I through direct and/or indirect mechanisms. The involvement of NK-1 in indirect induction of PPT-I by SCF is explained in a two-step mechanism: Concomitant induction of PPT-I and NK-1 followed by auto stimulation of the expressed, membrane bound NK-1 with the released peptides derived from PPT-I. Since PPT-I is implicated in several functions, we determined tissue-specific expression. Two relevant cell types, fibroblasts and epithelial cells, show cell-specific differences in reporter activity.

Also in accordance with the present invention, upstream regulatory sequences of the NK-2 gene and a gene encoding the SP receptor have been cloned. The control of expression of these genes is involved in the regulation of cell proliferation and malignancy.

The NK-1 receptor shares homology with regions of fibronectin, an extracellular matrix protein that is increased in patients with bone marrow fibrosis. It is shown herein that substance P (SP), the preferred ligand for NK-1, binds to fibronectin in the sera of patients with various categories of bone marrow fibrosis. SP is a fibrogenic factor produced by expression of the PPT-I gene and a stimulator of macrophages. As fibroblasts and macrophages are implicated in the pathophysiology of bone marrow fibrosis, it appears that SP is transported to the bone marrow and other organs via binding to fibronectin. Thus, in one embodiment of the present invention, use of PPT-I (the gene from which SP is derived) is utilized as a target for treatment of patients with bone marrow fibrosis. Since bone marrow fibrosis is secondary to myeloproliferative disorders, PPT-I and its receptor, and/or pathways associated with the products of these genes provide biological targets for the development of therapeutic agents for use in patients with myeloproliferative disorders.

As set forth in Example 5 below, cytosolic factors present in malignant cells enhance translation of a subset of genes. In accordance with the present invention, the identity and specificity of these translation enhancing factors is determined. Initially, it is ascertained which portions of the 3' sequence of PPT-I mRNA are important for the observed enhanced translation by the cytosolic extracts. Computer analyses can also be performed to assess the secondary folding of the mRNA for each PPT-I transcript. Different sequences can be incubated with cytosolic factors and then separated by gel shift. Specificity of competition can be verified with the antisense sequences and with sequences from other regions of PPT-I mRNA. Once the relevant sequences are identified, affinity columns can be prepared with the relevant nucleotides and the putative cytosolic factors isolated. The proteinaceous character of the factors can be confirmed followed by partial amino acid sequencing. Based on this sequence information, degenerate DNA probes can be synthesized and used to screen cDNA libraries to get the full length factor(s) coding sequence(s). In the event that interacting proteins are identified, the first isolate will be utilized to retrieve others using the yeast two hybrid system.

Thus, the present invention provides expression regulatory elements for several key proteins involved in cell proliferation. In addition, the discoveries made in accordance with the invention targets have revealed novel targets for development of therapeutic agents for the treatment of various forms of cancer, including myeloproliferative disorders, as well as bone marrow fibrosis. The sections below set forth various embodiments for practicing the present invention. To the extent that specific methods and/or reagents are specified, this is done for illustration only, and is not intended to limit the invention.

Polynucleotides

The polynucleotides of the present invention include isolated polynucleotides comprising the PPT-I, NK-2 and SP-R promoters and/or 3' untranslated region, and fragments, and polynucleotides closely related thereto. More specifically, the polynucleotides of the invention include a polynucleotide comprising the human nucleotide sequences contained in SEQ ID NO:1, SEQ ID NO: 2, SEQ ID NO:3 or SEQ ID NO:4, and polynucleotides having the particular sequence of SEQ ID NO:1, SEQ ID NO:2, SEQ ID NO:3 or SEQ ID NO:4. The polynucleotides further include a polynucleotide comprising a nucleotide sequence that is at least 70% identical to that of SEQ ID NO:1, SEQ ID NO:2, SEQ ID NO:3 or SEQ ID NO:4, over its entire length. In this regard, polynucleotides with at least 70% are preferred, more preferably at least 80% identity, even more preferably at least 90% identity, yet more preferably at least 95% identity, 97% are highly preferred and those with at least 98-99% are most highly preferred, with at least 99% being the most preferred. Also included are a nucleotide sequence which has sufficient identity to a nucleotide sequence contained in SEQ ID NO:1, SEQ ID NO:2, SEQ ID NO:3 or SEQ ID NO:4 to hybridize under conditions useable for amplification or for use as a probe or marker. The invention also provides polynucleotides which are complementary to such PPT-I, NK-2 and SP polynucleotides.

When the polynucleotides of the invention are used as regulatory elements for the recombinant production of PPT-I, NK-2 or SP-R polypeptide, or for a heterologous polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. The polynucleotide may also contain other non-coding 5' and 3' sequences, such as transcribed, non-translated sequences, splicing and polyadenylation signals, ribosome binding sites and sequences that stabilize mRNA.

Thus, this invention provides oligonucleotides (sense or antisense strands of DNA or RNA) having sequences capable of hybridizing with at least one sequence of a nucleic acid molecule of the present invention. Such oligonucleotides are useful as probes for detecting PPT-I, NK-2 or SP-R genes. In one preferred embodiment, oligonucleotides for use as probes or primers are based on rationally-selected nucleic acid sequences chosen from SEQ ID NO:1, SEQ ID NO:2, SEQ ID NO:3 or SEQ ID NO:4.

PPT-I, NK and SP-R polynucleotides of the present invention may be prepared by two general methods: (1) they may be synthesized from appropriate nucleotide triphosphates, or (2) they may be isolated from biological sources. Both methods utilize protocols well known in the art. The availability of nucleotide sequence information, such as the cDNA having SEQ ID NO:1, SEQ ID NO:2, SEQ ID NO:3, or SEQ ID NO:4, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides should be synthesized in stages, due to the size limitations inherent in various oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

PPT-I, NK-2 and SP-R genes (or portions thereof) and promoters also may be isolated from appropriate biological sources using methods known in the art. In the exemplary embodiment of the invention, PPT-I, NK-2 and SP-R may be isolated from genomic libraries of human. A preferred means for isolating PPT-I, NK-2 and SP-R genes is PCR amplification using genomic templates and sequence-specific primers. Genomic libraries are commerically available, and can also be made by procedures well known in the art. In positions of degeneracy where more than one nucleic acid residue could be used to encode the appropriate amino acid residue, all the appropriate nucleic acid residues may be incorporated to create a mixed oligonucleotide population, or a neutral base such as inosine may be used. The strategy of oligonucleotide design is well known in the art.

In accordance with the present invention, nucleic acids having the appropriate level sequence homology (i.e., 70% identity or greater) with part or all of SEQ ID NO:1 SEQ ID NO:2, SEQ ID NO:3 or SEQ ID NO:4 may be identified by using hybridization and washing conditions of appropriate stringency. For example, hybridizations may be performed, according to the method of Sambrook et al., using a hybridization solution comprising: 1.0% SDS, up to 50% formamide, 5×SSC (150 mM NaCl, 15 mM trisodium citrate), 0.05% sodium pyrophosphate (pH 7.6), 5× Denhardt's solution, and 100 microgram/ml denatured, sheared salmon sperm DNA. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes to 1 hour at 37° C. in 2×SSC and 0.1% SDS; (4) 2 hours at 45-55° C. in 2×SSC and 0.1% SDS, changing the solution every 30 minutes.

One common formula for calculating the stringency conditions required to achieve hybridization between nucleic acid molecules of a specified percent identity is set forth by (Sambrook et al., 1989, supra):

$$T_m = 81.5° C. + 16.6 \text{ Log[Na+]} + 0.41(\% G+C) - 0.63(\% \text{ formamide}) - 600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and wash in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and wash in 1×SSC and 0.5% SDS at 65° C. for 15 minutes. A very high stringency hybridization is defined as hybridization in 6×SSC, 5x Denhardt's solution, 0.5% SDS and 100 µg/ml denatured salmon sperm DNA at 42° C., and wash in 0.1×SSC and 0.5% SDS at 65° C. for 15 minutes.

Nucleic acid molecules of the invention include cDNA (where appropriate), genomic DNA, RNA, and fragments thereof which may be single or double stranded. Thus, this invention provides oligonucleotides having sequences capable of hybridizing with at least one sequence of a nucleic acid molecule of the present invention, such as selected segments of the DNA having SEQ ID NO:1, SEQ ID NO:2, SEQ ID NO:3 or SEQ ID NO:4. Primers capable of specifically amplifying the nucleic acids of the invention are described herein. As mentioned previously, such oligonucleotides are useful as probes and primers for detecting, isolating or amplifying PPT, NK-2 or SP-R genes.

Antisense nucleic acid molecules may be targeted to translation initiation sites, promoter regions, 3' untranslated regions and/or splice sites to inhibit the expression of the PPT-I, NK-2 or SP-R genes or production of the encoded polypeptides. Such antisense molecules are typically between 15 and 30 nucleotides in length and often span the translational start site of mRNA molecules. Suitable PPT-I antisense molecules for practicing this aspect of the invention include:

```
EXON 2:
GTG GAC ACA AGA AAA AAG ACT GCC A   (SEQ ID NO:5)

EXON 3:
GAA GAT GCT CAA AGG CGT CCG GCA G   (SEQ ID NO:6)

EXON 7:
ATA ATT CTG CAT TGC ACT CCT TTC AT. (SEQ ID NO:7)
```

Alternatively, antisense constructs may be generated which contain the entire PPT-I, NK-2 or SP-R promoters (or 3' untranslated region of PPT-I), with coding sequences operatively linked thereto, encoding the alternatively spliced PPT α, β, γ or δ proteins, NK-2 or SP-R proteins, in reverse orientation. Such antisense constructs are easily prepared by one of ordinary skill in the art.

It will be appreciated by persons skilled in the art that variants (e.g., allelic variants) of PPT-I, NK-2 or SP-R sequences exist in the human population, and must be taken into account when designing and/or utilizing oligonucleotides of the invention. Accordingly, it is within the scope of the present invention to encompass such variants, with respect to the nucleotide sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a human population. Such variants would not demonstrate altered PPT-I, NK-2 or SP-R regulatory activity. Additionally, the term "substantially complementary" refers to oligonucleotide sequences that may not be perfectly matched to a target sequence, but such mismatches do not materially affect the ability of the oligonucleotide to hybridize with its target sequence under the conditions described.

Nucleic acids of the present invention may be maintained as DNA in any convenient cloning vector. In a preferred embodiment, clones are maintained in plasmid cloning/ expression vector, such as pBluescript (Stratagene, La Jolla, Calif.), which is propagated in a suitable E. coli host cell.

The polynucleotides may be used for a variety of purposes in accordance with the present invention. DNA, RNA, or fragments thereof may be used as probes to detect the presence of and/or expression of PPT-I, NK-2 or SP-R genes. Methods in which PPT-I, NK-2 or SP-R nucleic acids may be utilized as probes for such assays include, but are not limited to: (1) in situ hybridization; (2) Southern hybridization (3) northern hybridization; and (4) assorted amplification reactions such as polymerase chain reaction (PCR).

The PPT-I, NK-2 and SP-R nucleic acids may also be utilized as probes to identify related genes from other species. As is well known in the art, hybridization stringencies may be adjusted to allow hybridization of nucleic acid probes with complementary sequences of varying degrees of homology.

The PPT-I, NK-2 and SP-R nucleic acids of the present invention can be used to identify and isolate other members of the growth regulatory pathway(s) in which PPT-I, NK-2 or SP-R is involved. A yeast two-hybrid system can be used to identify proteins that physically interact with the PPT-I, NK-2 or SP-R protein, as well as isolate their nucleic acids. In this system, the coding sequence of the protein of interest is operably linked to the coding sequence of half of an activator protein. This construct is used to transform a yeast cell library which has been transformed with DNA constructs that contain the coding sequence for the other half of the activator protein operably linked to a random coding sequence from the organism of interest. When the protein made by the random coding sequence from the library interacts with the protein of interest, the two halves of the activator protein are physically associated and form a functional unit that activates the reporter gene. In accordance with the present invention, all or part of the human PPT-I, NK-2, or SP-R promoter or 3' end and/or coding sequence may be operably linked to the coding sequence of the first half of the activator, and the library of random coding sequences may be constructed with cDNA from human and operably linked to the coding sequence of the second half of the activator protein. Several activator protein/reporter genes are customarily used in the yeast two hybrid system, the Gal4/LacZ system (see Clark et al., 1998 PNAS 95:5401-5406), among others.

Vectors, Host Cells, and Expression

The present invention also relates to vectors which comprise a polynucleotide or polynucleotides of the present invention, and host cells which are genetically engineered with vectors of the invention and to the production of gene products by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells. The selection of an appropriate host is deemed to be within the scope of those skilled in the art from the teachings herein.

A number of cell lines are particularly suited for the present invention and may be purchased from American Type Culture Collection (ATCC), Rockville, Md. These highly preferred cell lines are ZR7530, infiltrating ductal carcinoma from ascites fluid; BT474, ductal carcinoma; T47D, ductal carcinoma from pleural effusion; MDAMB330, breast carcinoma from pleural effusion; 184B5, chemically transformed mammary epithelial; DU4475 breast carcinoma; BT 483, ductal carcinoma; MCF12A, nontransformed mammary epithelial cells; Hs578Bst, normal breast epithelial cells; CCL64, Mink Lung epithelial; L929, murine fibroblast; and MDBK, bovine epithelial kidney cell. All cell lines were cultured according to ATCC instructions.

Undifferentiated neuroblastoma cells, SH-SY5Y obtained from the Department of Biochemistry, UMDNJ—New Jersey Medical School, Newark, N.J. are particularly preferred for certain aspects of the present invention. SH-SY5Y cells should be cultured in DMEM with high glucose (Life Technologies, Grand Island, N.Y.) containing 10% FCS (Hyclone Laboratories, Logan, Utah). Skin fibroblasts (CRL 1502) and normal mammary epithelial cells (MCF-10 and MCF-12A) may be purchased from American Type Culture Collection (Manassas, Va.). Cells should be cultured based on their instructions.

More particularly, the present invention also includes recombinant constructs comprising one the promoter or 3' regulatory sequences of the invention. The constructs comprise a vector, such as a plasmid or viral vector, into which is inserted a DNA construct comprising a coding sequence operably linked to one of the regulatory sequences of the invention. Large numbers of suitable vectors are known to those of skill in the art, and are commercially available. A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, herpes viruses including HSV and EBV, and retroviruses. Many gene therapy protocols in the prior art have employed disabled murine retroviruses. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWL-NEO, pSV2CAT, pOG44, pXT1, pSG (Stratagene) pSVK3, pBPV, pMSG, pSVL (Pharmacia). However, any other plasmid or vector may be used as long as they are replicable and viable in the host. In addition, a complete mammalian transcription unit and a selectable marker can be inserted into a prokaryotic plasmid. The resulting vector is then amplified in bacteria before being transfected into cultured mammalian cells. Examples of vectors of this type include pTK2, pHyg and pRSVneo.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

Detection of PPT-I Encoding Nucleic Acids and Assay Methods for Identifying Mutations, Antagonists and Agonists Affecting PPT-I Gene Expression In accordance with the present invention, PPT-I expression has been found to be upregulated in breast cancers. Mutations in the promoter region or the coding sequence of PPT-I are associated with the malignant phenotype. On one aspect of the invention, the PPT-I promoter and coding sequence isolated from cancer cells are screened for mutations. Currently, the most direct method for mutational analysis is DNA sequencing, however it is also the most labor intensive and expensive. It is usually not practical to sequence all potentially relevant regions of every experimental sample. Instead, some form of preliminary screening method is commonly used to identify and target for sequencing only those samples that contain mutations. Single stranded conformational polymorphism (SSCP) is a widely used screening method based on mobility differences between singlestranded wild type and mutant sequences on native polyacrylamide gels. Other methods are based on mobility differences in wild type/mutant heteroduplexes (compared to control homoduplexes) on native gels (heteroduplex analysis) or denaturing gels (denaturing gradient gel electrophoresis). Sample preparation is relatively easy in these assays, and conditions for electrophoresis required to generate the often subtle mobility differences that form the basis for identifying the targets that contain mutations are well known to those of skill in the art. Another parameter to be considered is the size of the target region being screened. In general, SSCP is used to screen target regions no longer than about 200-300 bases.

Another type of screening technique currently in use is based on cleavage of unpaired bases in heteroduplexes formed between wild type probes hybridized to experimental targets containing point mutations. The cleavage products are also analyzed by gel electrophoresis, as subfragments generated by cleavage of the probe at a mismatch generally differ significantly in size from full length, uncleaved probe and are easily detected with a standard gel system. Mismatch cleavage has been effected either chemically (osmium tetroxide, hydroxylamine) or with a less toxic, enzymatic alternative, using RNase A. The RNase A cleavage assay has also been used, although much less frequently, to screen for mutations in endogenous mRNA targets for detecting mutations in DNA targets amplified by PCR. A mutation detection rate of over 50% was reported for the original RNase screening method.

Another method to detect mutations in DNA relies on DNA ligase which covalently joins two adjacent oligonucleotides which are hybridized on a complementary target nucleic acid. The mismatch must occur at the site of ligation. As with other methods that rely on oligonucleotides, salt concentration and temperature at hybridization are crucial. Another consideration is the amount of enzyme added relative to the DNA concentration. In summary, exemplary approaches for detecting alterations in PPT-I nucleic acids or polypeptides/proteins include:

a) comparing the sequence of nucleic acid in the sample with the wild-type PPT-I nucleic acid sequence to determine whether the sample from the patient contains mutations; or b) determining the presence, in a sample from a patient, of the polypeptide encoded by the PPT-I gene and, if present, determining whether the polypeptide is full length, and/or is mutated, and/or is expressed at the normal level; or c) using DNA restriction mapping to compare the restriction pattern produced when a restriction enzyme cuts a sample of nucleic acid from the patient with the restriction pattern obtained from normal PPT-I gene or from known mutations thereof; or, d) using a specific binding member capable of binding to a PPT-I nucleic acid sequence (either normal sequence or known mutated sequence), the specific binding member comprising nucleic acid hybridizable with the PPT-I sequence, or substances comprising an antibody domain with specificity for a native or mutated PPT-I nucleic acid sequence or the polypeptide encoded by it, the specific binding member being labeled so that binding of the specific binding member to its binding partner is detectable; or, e) using PCR involving one or more primers based on normal or mutated PPT-I gene sequence to screen for normal or mutant PPT-I gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

In most embodiments for screening for susceptibility alleles, the PPT-I nucleic acid in the sample will initially be amplified, e.g. using PCR, to increase the amount of the analyte as compared to other sequences present in the sample. This allows the target PPT sequences to be detected with a high degree of sensitivity if they are present in the sample. This initial step may be avoided by using highly sensitive array techniques that are becoming increasingly important in the art.

The identification of the PPT-I gene's association with cancer and hematopoietic diseases paves the way for aspects of the present invention to provide the use of materials and methods, such as are disclosed and discussed above, for establishing the presence or absence in a test sample of a variant form of the gene, in particular an allele or variant specifically associated with cancer or hematopoietic diseases. This may be for diagnosing a predisposition of an individual to cancer or hematopoietic disease. It may be for diagnosing cancer or hematopoietic disease in a patient with the disease as being associated with an altered or aberrantly regulated PPT-I gene.

This allows for planning of appropriate therapeutic and/or prophylactic measures, permitting stream-lining of diagnosis, treatment and outcome assessments. The approach further stream-lines treatment by targeting those patients most likely to benefit.

According to another aspect of the invention, methods of screening drugs for therapy, i.e., for restoring or inhibiting PPT-I product functions are provided.

The PPT-I polynucleotides and fragments can be employed in drug screening assays, and may either be free in solution, affixed to a solid support or within a cell. One method of drug screening utilizes a PPT-I promoter/reporter gene construct, preferably in competitive binding assays. Such cells, either in viable or fixed form, can be used for standard binding assays. One may determine, for example, formation of complexes between a PPT-I promoter and the agent being tested, or examine the degree to which the formation of a complex between a PPT-I polypeptide or fragment and a known ligand is interfered with by the agent being tested.

In a particularly preferred embodiment of the invention, the promoter region or 3' region of the PPT-I gene is operatively linked to a reporter gene. Reporter genes suitable for this purpose include, without limitation, beta galactosidase, luciferase, chloramphenicol acetyltransferase, and green fluorescent protein. Methods for operably linking the coding regions for the reporter genes to the PPT-I regulatory sequences are well known to those of ordinary skill in the art.

Following introduction of such DNA constructs into recipient host cells, the cells may be contacted with agents suspected of affecting expression of the reporter gene. Agents capable of altering expression of the reporter gene may prove efficacious in regulating PPT-I expression, thereby having therapeutic advantage in the treatment of cancer or other disorders where altered PPT-I expression plays a role.

Pharmaceuticals and Peptide Therapies

The discovery that PPT-I gene expression is altered in cancer or hematopoietic diseases facilitates the development of pharmaceutical compositions useful for treatment and diagnosis of these syndromes and conditions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

The following examples are provided to describe the invention in greater detail. They are intended to illustrate, not to limit, the invention.

EXAMPLES

Materials and Methods Utilized in the Examples

Goat antihuman (h) SCF, antihIL6, SCF and IL6 were purchased from R&D Systems (Minneapolis, Minn.). Rabbit antihIL1a and rabbit antiSP were purchased from Endogen (Boston, Mass.) and Arnel Products Co., Inc. (NY, N.Y.) respectively. Alkaline phosphatase (AP)conjugated goat antirabbit IgG and AP goat antimouse IgG were purchased from Kirkegaard & Perry Laboratories Inc. (Gaithersburg, Md.). APconjugated swine antigoat IgG was obtained from Boehringer Mannheim Biochemicals (Indianapolis, Ind.). Hoffman LaRoche (Nutley, N.J.) provided rhIL1∝.

Reagents

For purposes of the present invention, Substance P, streptavidin and bovine serum albumin (BSA) may be purchased from readily available commercial sources such as Sigma (St. Louis, Mo.). Substrate for alkaline phosphatase, 5-bromo-4-chloro-3-indolylphosphate/nitroblue tetrazolium (BLIP/NBT) was obtained from Kirkegaard and Perry Laboratories. CP-96,345-1 is commercially available from sources such as Pfizer, Inc. (Groton, Conn.). SR 48968 is commercially available from sources such as Sanofi Recherche (Montpellier Cedex, France).

Quantitation of SP-IR

Competitive ELISA quantitated SP-IR in supernatants from breast cancer cell cultures that were 80% confluent. Cell-free supernatants were stored in siliconized tubes at −70° C. until ready to be assayed. Streptavidin, 100~ml at 5 g/ml in distilled water, was added to Immulon 96-well plates (Dynatech Laboratories Inc., Chantilly, Va.). Streptavidin was allowed to dry at 37° C. After this, wells were blocked with 5% nonfat dry milk for 2 hr at room temperature and then washed with PBS containing 0.1% Tween-20 (PBST). Chiron Mimotopes (Emeryville, Calif.) synthesized biotinylated-SP, with spacer arm. Stock solution was diluted in 0.1% (v/v) acetic acid at 5 mg/ml, aliquoted in siliconized tubes and stored at −70° C. Working solution was diluted at 750 ng/ml with PBS containing 0.1% (w/v) BSA and 0.1% (w/v) sodium azide. Biotinylated-SP (100 ml) was added to wells and plates incubated for 1 hr at room temperature. Plates were washed (×4) with PBST. Competition by the mobilized and soluble SP for anti-SP forms the basis for the next step. Equal volume (50 µl) of optimum rabbit anti-SP (1/15,000), and unknown or standard solution were added to wells. Plates were incubated at room temperature for 1 hr. Each unknown was assayed in triplicate as undiluted and three serial dilutions. Bound anti-SP was detected by incubating for 1 hr with optimum (150 ng/ml) AP-goat antirabbit IgG. Color was developed with Sigma 104 phosphatase substrate as described (Rameshwar, P. et al. (1996), *Blood* 88, 98-106). A standard curve was developed with O.D. (405 nm) versus 12 serial dilutions of standard SP that ranged from 100 to 0.08 ng/ml. Quadruplicate wells with controls included total (anti-SP and PBS) and background color (anti-SP omitted).

Quantitative RT-PCR

In one embodiment of the present invention, quantitative RT-PCR was performed with total RNA extracted from breast cancer cells. Total RNA (2 pg) was subjected to reverse transcription (RT) in 25 µl for 1 hr at 42° C. Following reverse transcription, the reaction was stopped at 94° C. for 5 mins. RT mixture contained 50 mM Tris (pH 8.3), 30 mM KCl, 6 mM $MgCl_2$, 30 U M-MLV-RT (Boehringer Mannheim Biochemicals), 10 mM dithiothreitol, 40 U RNase inhibitor (Perkin Elmer-Cetus, Norwalk, Conn.), 5 µM random hexamer (Life Technologies, Grand Island, N.Y.) and 3.0 mM dNTP (Boehringer Mannheim Biochemicals). Competitive PCR was performed in 50 µl volume with 200 ng unknown cDNA and various log-fold dilutions of standard DNA ($10^{-2}$ $10^{-6}$ attomole/L). PCR reactions contained 20 mM Tris (pH 8.4), 10 mM KCl, 2 MM $MgCl_2$, 0.8 mM dNTP, 0.4 µM of each primer and 2.5 U Taq DNA Polymerase (Perkin ElmerCetus). Samples were overlaid with oil and then amplified for 35 cycles in a DNA thermal Cycler 480 (Perkin Elmer-Cetus). The profile for each cycle was 95° C. for 30 sec, 60° C. for 30 sec and 72° C. for 1 min. Reactions were subjected to a final extension at 72° C. for 7 min. PCR products (10 µl) were separated by electrophoresis on 1.5% agarose containing ethidium bromide. Band intensities were quantitated with a Fluorimager (Molecular Dynamics, Sunnyvale, Calif.) and data analyzed with the ImageQuant software. Amplicon sizes were verified by comparison with either 1 kb DNA ladder, DNA/Hind III fragments or low DNA mass ladder, all purchased from Life Technologies. DNA standards were prepared with PCR MIMIC construction kit, purchased from Clontech (Palo Alto, Calif.). Gene-specific nucleotides were synthesized at the Molecular Resource Facility, UMDNJ—New Jersey Medical School (Newark, N.J.) with an ABI model 392

DNA/RNA synthesizer (ABI, Foster City, Calif.). Acceptable primers for PPT-I include, for example.

```
                                              (SEQ ID NO:8)
   5'AAT TTA CCT GTC ATT GCC C3' (sense) and (SEQ ID NO:9)
   5-AGC CCT TTG AGC ATC TTC 3 (antisense) span
```

Exons 3 and 7 of α-, β and γ-PPT-I with sizes equivalent to 261 bp, 315 by and 270 by respectively (Harmar, A. J. et al., *FEBS Lett.* 208, 67-72). PPT-I standard of 157 base pairs in length was constructed with the following: primer pair, 20 gene-specific nucleotides adjacent to each primer and, MIMIC DNA in the center. Standard NK-2 of 150 base pairs in length was constructed as for PPT-I with primers designed from the cloned cDNA and span 274 by Gerard, N. P. et al, *J. Biol. Chem.*, 265 20455-20462.

NK-2 primers suitable for the invention include:

```
                                              (SEQ ID NO:10)
   sense,     5'AGT CTC CTT ACT GTG ACA CC 3'; and (SEQ ID NO:11)
   antisense  5'CTA CCA CCT CTA CTT CAT CC 3'.
```

NK-1 primers suitable for the invention include

```
   sense,     5'CTG CTG GAT AAA CTT CTT CAG GTA G-3'    (SEQ ID NO:12)

antisense, 5'AGG ACA GTG ACG AAC TAT TTT CTG G 3'.   (SEQ ID NO:13)
```

In a second embodiment of the present invention, bone marrow stroma was stimulated in serum-free α-MEM supplemented with Insulin-transferrin-selenium-A (Life Technologies). Quantitative RT-PCR with total RNA, extracted from bone marrow stroma and construction of standard DNA was performed as described in Singh, D., supra. The end sequences of the standard DNA contained gene-specific sequences that are complementary for the reaction primers. The primers in the standard DNA flank neutral DNA. Total RNA (2 μg) was reverse transcribed and 200 ng cDNA used in PCR with specific oligonucleotide primers for PPT-I, NK-1 or NK-2. Standard DNA, $\log_{10}$ fold dilutions, ranged between $10^{-2}$ to $10^{-6}$ attomole/L. Each unknown sample was assayed with a particular concentration of standard DNA in the same reaction tube. PCR products (10 μl) were separated by electrophoresis on 1.5% agarose containing ethidium bromide and the densities of the DNA bands quantitated with a Fluorimager (Molecular Dynamics, Sunnyvale, Calif.) and then analyzed with ImageQuant software. A standard curve was established for each unknown sample: band densities of unknown/standard DNA vs. $\log_{10}$ standard DNA concentration was used to determine the concentration of RNA molecules in the unknown samples. The concentration of the unknown sample was selected at the concentration in which the ratio of the unknown and standard were equivalent.

Preparation of Bone Marrow Stroma

In the present invention, bone marrow stroma was prepared by first obtaining bone marrow aspirate from the posterior iliac crest of normal healthy volunteers after obtaining informed consent. Bone marrow cells were cultured in 25 cmz tissue culture flasks (Falcon 3109, Becton Dickinson Labware, Lincoln Park, N.J.) at 33° C. for 3 days. After three days, granulocytes and red cells were removed by FicollHypaque (Sigma) density gradient. The mononuclear fraction was replaced into flasks. Cultures were reincubated until confluence with weekly replacement of 50% stromal medium.

Stimulation of Bone Marrow Stroma

Transfected bone marrow stroma was stimulated with optimal concentrations of IL-1α (2.5 ng/ml), SCF (8 ng/ml) or 1 nM substance P, SP (Sigma, St Louis, Mo.) and/or 10 nM NK-1-specific antagonist (CP-99,994) in α-MEM with 2% FCS. In other embodiments, bone marrow stroma was stimulated with 5 μg/ml forskolin, FK (Sigma) for 2 and 5 h. SCF was purchased from R&D Systems (Minneapolis, Minn.) and IL-1α was obtained from Hoffman LaRoche, Nutley, N.J. Pfizer, Inc. (Groton, Conn.) provided CP-99, 994. Substance P and CP-99,994 were dissolved and stored as described in Ramewshwar et al (1996), supra. Optimal parameters were determined with dose-response and time-course studies.

Isolation of Poly A RNA

Confluent bone marrow stroma was stimulated with 25 ng/ml rhIL-1α or 10 ng/ml SCF for 24 h. Poly A RNA was isolated from total RNA by selection (2×) on oligo-dT cellulose (Life Technologies). The cellulose column was washed once with 10 mM Tris, pH 7.0; 0.5 M NaCl; 1M EDTA and once with 10 mM Tris, pH 7.0; 0.2 M NaCl; 1M EDTA. Poly A RNA was eluted with 10 mM Tris (pH 7.0) and 1M EDTA. RNA was precipitated by standard techniques and then resuspended in DEPC-treated water. The purity was verified by the absence of rRNA.

In vitro Translation

In vitro translation for PPT-I was performed with poly A RNA from stroma stimulated with IL-1a or SCF (Rameshwar, P., et al., *Leuk. Lymphoma* 18, 1-10; Merrill, J. E. et al., *FASEB J.* 9, 611-618). As verified by quantitative RT-PCR, IL-1α and SCF induced 250,100±980 (n=6) and 134,340±545 (n=6) molecules of β-PPT-I/μg poly A, respectively. We verified the presence of IL-1a, IL6 and SCF mRNA in each preparation of poly A RNA (n=3) by northern analysis. Translation reactions were performed in siliconized tubes with 50 μl of the following: rabbit reticulate lysate system (Promega, Madison, Wis.), 0.5 μg poly A RNA, 20 μM Met-free amino acid mixture (Promega) and 40 μCi L [$^{35}$S] Met (>1,000 Ci/mmol, Dupont/New England Nuclear). Reactions were incubated for 16 hr at 30° C. Parallel reactions contained cytosolic extracts from breast cancer cell lines or MCF12A. Cytosolic extracts were prepared from 10' cells in a final volume of 0.5 ml as described in Rameshwar, P. et al., *Immunol.* 153, 2819-2830. Positive reactions contained Luciferase RNA (Promega). Background/negative reactions contained water instead of poly A RNA.

Quantitation of SP-IR, SCF, IL-6 and IL-1α was performed by ELISA using 2 μl of reaction mixture. The remaining mixture was used for immunoprecipitation of SP. Proteins were precipitated in the 2 μl sample with trichloroacetic acid (Sigma). Precipitates were pelletted, washed (5×) with PBS, dried, redissolved in 10 μl of sterile distilled water and then quantitated for total proteins using a microassay (BioRad, Hercules, Calif.). SP-IR levels are expressed per µg poly A RNA.

Immunoprecipitation and Western Blot

Immunoprecipitation and western blots were performed as described (Rameshwar et al. 1994, supra). Briefly, equivalent protein (1 µg) from each translational reaction was incubated at 4° C. overnight with anti-SP (1/15,000), anti-hSCF (1 ng/ml), anti-IL-1α (1 mg/ml) or anti-hIL-6 (1 mg/ml). Control reactions were incubated with nonimmune species-specific IgG. Immune complexes were selected by incubating at 4° C. for 6 hr with protein A sepharose CL 4B (Sigma). Following incubation with protein A, centrifugation of the sepharose was performed at 4° C. for 30 min at 10,000 g. Pellets were washed with PBS, resuspended in sample buffer and then electrophoresed on 16% SDS-PAGE. Positive control lanes contained SP, IL-1α or SCF. Proteins were electrophoretically transferred to Immobilon-P membranes (Millipore, Bedford, Mass.) and then incubated with anti-SP (1/15,000), anti-SCF (1 ng/ml), anti-IL-6 (1 mg/ml) or anti-IL-1α (1 mg/ml). Membranes were washed and then incubated with the appropriate AP-conjugated second antibody (50 ng/ml). Color was developed with BCIP/NBT. The $M_r$ of developed bands was compared with prestained low range protein standards (Diversified Biotech, Newton Centre, Mass.).

DNA-binding proteins were extracted from transfected stromal cells using a rapid micro preparation technique as described (Andrews, N. D. et al. 1997, *Nuc. Acids Res* 19:2499). Protein extraction for endogenous CRE-binding proteins were performed by boiling for 5-10 mins in 100 mM Tris and 4% SDS. Protein concentrations were determined using BioRad DC protein assay. Proteins were separated on 15% SDS-PAGE and then transferred to PVDF transfer membrane (NEN). Membranes were incubated overnight with rabbit anti-CREM, anti-phospho-CREB (Cell Signaling, Beverly, Mass.) or anti-CREB (Cell Signaling). The working dilutions of antibodies were at 1/1000. Anti-CREM cross-reacts with the different isoforms of CREM proteins and ICER. At the end of the incubation period with the primary antibody, membranes were washed and then incubated with HRP-conjugated goat anti-rabbit IgG (1/5000) for 45 mins. HRP was developed with ECL western blotting detection reagents (Amersham Pharmacia Biotech Inc, Piscataway, N.J.).

Transfection and Reporter Gene Assay pGL3-basic with inserts of different fragments from PPT-I-p1.2 was co-transfected with pβ-gal-Control (0.5 µg each) in 80% confluent bone marrow stroma using SuperFect (Qiagen, Valencia, Calif.). After 48 h cells were scraped in 30 µl 250 mM Tris (pH 8.0) and then lysed by freezing and thawing in a dry ice/ethanol bath. Cell-free lysates (24 µl) were obtained by centrifugation at 15,000 g for 5 min at 4° C. and then diluted with 5× cell culture lysis buffer (Promega). Luciferase and β-gal activities were quantitated with 10 µl of lysates using Luciferase assay system (Promega) and Luminescent β-galactosidase detection kit II (Clontech) respectively. In the experimental model, the ratios of Luciferase/β-gal in cells transfected with vector alone ranged from 0.18 to 0.19 and was normalized to 1. Because cytokines induce the promoter upstream of β-gal, in cytokine-stimulated cells, luciferase activity was presented/mg of total protein with the levels normalized with stroma transfected with vector alone. Total protein was determined using standard techniquees well known in the art.

CRE and CRE-like Mutation

Mutations were performed with a mutagenesis kit (Stratagene, La Jolla, Calif.). The desired mutant sequences (Table 1) were synthesized within 40 nt in the forward and reverse directions and then used in PCR with pGL3 containing wild type Upstream/N0. After PCR amplification, mutation was verified by identification of Apa L1 within CRE-like mutant and the loss of Xho 1 in CRE mutant.

Electrophoretic Mobility Shift Assay

Mutant or wild type CRE and CRE-like sequences, 20 ng (Table 1) were end labeled with $\gamma$-$^{32}$P-ATP using T4 polynucleotide kinase. Labeled probe was incubated with 2 µg of CREMτ or ICERIIγ in the presence or absence of excess cold competitor for 1 h. Reactions were separated on 4% PAGE, which were dried and then developed by autoradiography after 24 h.

In situ Hybridization

In situ hybridization was performed as described (Rameshwar, P. et al. (1998), *Am. J. Hematol.* 59, 133-142). For each transcript, hybridization was performed with a cocktail of three antisense biotinylated oligonucleotides, each 18 nucleotides in length. Suitable oligonucleotides include, but are not limited to, NK-1, nucleotides 67-84, 439-456 and 815-832; NK-2, nucleotides 151-168, 712-729 and 1001-1018; β-PPT-I, nucleotides 210-227, 350-367 and 429-446.

Paraffin sections, 4 µm, from breast biopsies were placed on Superfrost/Plus slides (Fisher Scientific, Springfield, N.J.). Sections were deparaffinized by the following sequential steps: 56° C. overnight, xylene (2×5 min), 99% ethanol (2×1 min), 95% ethanol (2×1 min) and DEPC-treated water (1×5 min). All incubations were performed at room temperature. This was followed by rehydration in 2×SSC at 37° C. for 30 min. Sections were washed with DEPC-treated water for 5 min at room temperature and then incubated with 30 µg/ml proteinase K for 1 hr at 37° C. Negative control slides were incubated with 100 µg/ml RNase for 30 min at 37° C. Enzyme activities were stopped with 0.4% paraformaldehyde in PBS. Cells were prehybridized at 37° C. for 1 hr in equal volumes of prehybridization solution (5 Prime 3 Prime, Boulder, Colo.) and formamide, and 10 mg/ml salmon sperm (5 Prime 3 Prime). Cells were hybridized at 37° C. for 24 hr with 200 ng/ml of oligonucleotide cocktail. Following hybridization, sections were washed sequentially for 5 min at 37° C. in the following buffers: 4×SSC/30% formamide, 2×SSC/30% formamide and 0.2×SSC/30% formamide. Sections were next incubated for 1 hr at room temperature with 1.25 µg/ml avidinAP (Boehringer Mannheim Biochemicals). Control slides were incubated with a cocktail of sense oligomers. AP was developed with BLIP/NBT. Slides were counterstained with Harris Modified Hematoxylin (Fisher Scientific) and then examined with an Olympus Bx40 microscope (New Jersey Scientific, Inc., Middlebush, N.J.).

In situ hybridization for the luciferase reporter vector, pGL3 (Promega, Madison, Wis.) was performed with a 300 bp ampicillin DNA probe, which was labeled with a random biotin labeling kit (NEN, Boston, Mass.). Probe was prepared by PCR with primers specific for ampicillin gene and pSEAP2 (Clontech, Palo Alto, Calif.) as template. The second labeling was performed with antibodies for the three major stromal subsets as described. Primary antibodies for fibroblast, endothelial cells and macrophages were specific for prolyl 4-hydroxylase (Dako, Carpinteria, Calif.), von Willebrand factor (Dako) and CD14. After this, cells were incubated for 30 mins with rat PE-conjugated anti-κ (Becton Dickinson Immunocytometry Systems, San Jose, Calif.) and FITC-avidin (Vector Laboratories, Burlingame, Calif.). Cells were examined for fluorescence intensity with excitation at 495 nm/emission at 515 nm for FITC and excitation at 595 nm/emission at 606 nm for PE.

Cell Proliferation

Clonogenic assays studied the proliferation of breast cancer cell lines. Duplicate cultures were performed with $10^3$ cells/ml in 1.2% methylcellulose matrix that contained various concentrations (between about 100 to 0.001 mM) of NK-1, NK-2 or (NK-1+NK-2) antagonists. Baseline cultures contained media alone. For each cell line, the assay contained the appropriate culture media. Cultures were incubated for 2 wk at 37° C. This was followed by enumeration of colonies that contained more than 10 cells. In a highly preferred embodiment, the concentration of antagonist is 1 nM.

Statistical Analysis

Data were analyzed using analysis of variance and Tukey-Kramer multiple comparisons test and the Students ttest to determine the significance (P value) between experimental values. A P value of <0.05 was considered significant.

Example 1

Expression of PPT-I, NK-1 and NK-2 in Breast Cancer Cells

We studied PPT-I, NK-1 and NK-2 expression in breast cancer cell lines and breast biopsies. In the initial studies, we determined the production of SP-R by breast cancer cells, nontransformed mammary epithelial cell lines and unrelated cell lines, CCL64, MDBK and L929. As shown in Table 1, SP levels were more than 7 fold higher in breast cancer cells than nontransformed mammary epithelial cells and SP was not detected in the culture media of the unrelated cell lines. As Substance P is the major PPT-I peptide product, its high levels prompted us to determine whether enhanced production of SP correlated with steady state PPT-I mRNA using quantitative RT-PCR.

TABLE 1

Production of immunoreactiveSP (SP-IR) by breast cancer cell lines.

| Cell Lines | SP-IR (ng/ml) |
|---|---|
| Transformed | |
| MDAMB330 | 146 + 5 |
| T47D | 209 + 38 |
| ZR7530 | 159 + 12 |
| BT474 | 160 + 16 |
| DU4475 | 90 + 3 |
| BT483 | 102 + 8 |
| 184B5 | 64 + 8 |
| Nontransformed | |
| MCF12A | 9 + 2 |
| Hs578Bst | 8 + 1 |
| Other | |
| CCL64 | <0.08 |
| L929 | <0.08 |
| MDBK | <0.08 |

ELISA quantitated SP-R in the culture media of breast cancer cell lines. Details of the technique are described in above. Each point is the mean (+SD) of 8 different cell passages.

The PPT-I gene consists of seven exons that can be alternately spliced into four transcripts (Harmar, A. J. et al., supra). Since each PPT-I transcript contains exons 3 and 6 (Harmar, A. J. et al., supra), we designed oligonucleotide primers that span these two exons. In each RT-PCR reaction, we observed single fragments equivalent to 315 base pairs, consistent with PPT-I (Harmar, A. J. et al., supra). The average levels of β-PPT-I in the breast cancer cell lines were 53 molecules/g total RNA, as shown in Table 2. As also described in Table 2, nontransformed mammary epithelial cells showed undetectable PPT-I, <1 molecule/g total RNA. The results indicate that PPT-I is highly expressed in breast cancer cell lines and that the predominant transcript is β-PPT-I.

We next determined if the receptors for PPT-I peptides were also increased. As shown in Table 2, quantitative RT-PCR NK-1 and NK-2 mRNA levels were increased in malignant cells. NK-1 mRNA was undetected in nontransformed mammary epithelial cells, but NK-2 mRNA was elevated (Table 2). Table 2 also describes that in four breast cancer cell lines, NK-2 levels were significantly (p<0.5) less than MCF12A and Hs578Bst cells. In other words, in contrast to nontransformed mammary epithelial cells which show an increase in NK-2 mRNA alone, breast cancer cells have significantly high levels of PPT-I, NK-1 and NK-2 mRNA (p<0.05).

TABLE 2

Levels of β-PPT-I, NK-1 and NK-2 mRNA in Breast Cancer cell lines.

| Cell Lines | β-PPT-I | NK-1 (molecules/µg total RNA) | NK-2 |
|---|---|---|---|
| Transformed | | | |
| MDAMB330 | 45 ± 3 | 1686 ± 52 | 4740 ± 40 |
| T47D | 65 ± 2 | 2600 ± 48 | 3768 ± 30 |
| ZR7530 | 42 ± 1 | 25 + 2 | 1218 + 25* |
| BT474 | 57 ± 4 | 28 ± 6 | 429 ± 22* |
| DU4475 | 55 ± 3 | 38 ± 8 | 389 ± 20* |
| BT 483 | 62 ± 5 | 1240 ± 35 | 560 ± 25* |
| Nontransformed | | | |
| MCF12A | <1 | <1 | 2419 ± 28 |
| Hs5782st | <1 | <1 | 2225 ± 44 |

Levels of β-PPT-I, NK-1 and NK-2 mRNA were determined by quantitative RT-PCR using total RNA (2 pg) from malignant or nontransformed mammary epithelial cells. For each cell line, quantitations were performed with RNA extracted from ten different passages. *p < 0.05 vs. nontransformed cells Example 2

Expression of PPT-I, NK-1 and NK-2 in Breast Biopsies

Because cell lines undergo multiple passages, we next determined whether PPT-I, NK-1 and NK-2 are similarly expressed in malignant breast biopsies. Comparison was made with benign tissue. By in situ hybridization, we determined that PPT-I, NK-1 and NK-2 are expressed in all malignant tissues. In benign tissues, PPT-I and NK-1 mRNA were not detected, whereas NK-2 mRNA was dense in benign tissue. No signal was detected with breast tissues (malignant and benign) hybridized with sense oligonucleotides. Parallel immunohistochemical studies indicated that malignant tissues were positive for SP-R and negative in benign tissues. Qualitative observations of the signals presented by in situ hybridization and the data shown for breast cancer cell lines in Tables 2 and 3 indicate comparable expression of PPT-I, NK-1 and NK-2 in malignant breast biopsies and breast cancer cell lines.

Example 3

Translational Rate of β-PPT-I mRNA

Although increased, the levels of PPT-I mRNA in breast cancer cells (Table 2) could not explain the high SP levels (Table 1). We next investigated if the increase in SP-R may be due to increased translation of β-PPT-I using an in vitro assay that contained soluble cytosolic extracts from either breast cancer cells or MCF12A. Since IL-1 induces PPT-I in bone marrow stroma (Ramewshar, P. (1997), supra; Merrill, J. E., supra), poly A RNA from IL-1 stimulated bone marrow stroma was used as PPT-I mRNA containing substrate. Before each assay, we verified the level of PPT-I mRNA in quantitative RT-PCR. Since each PPT-I transcript can produce Substance P (Harmar, A. J. et al., supra), its level was used as the read out to study the rate of PPT-I mRNA translation. In six different experiments (±SD), we found that SP-IR was increased 40±3 and 30±2 fold more in the presence of cytosolic extracts from breast cancer cells than extracts from MCF12A (Table 3).

TABLE 3

ImmunoreactiveSP (SP-IR) following in vitro translation.

| Cytosolic Extracts | SP-IR | IL1α | IL6 (pg/µg poly A RNA) | SCF |
|---|---|---|---|---|
| Transformed | | | | |
| MDAMB330 | 3146 ± 45 | 20 ± 6 | 230 ± 22 | 6 ± 1 |
| T47D | 2750 ± 28 | 10 ± 2 | 435 ± 25 | 5 ± 2 |
| ZR7530 | 3590 ± 42 | 5 ± 1 | 342 ± 34 | 8 ± 2 |
| BT474 | 3650 ± 36 | 12 ± 3 | 156 ± 21 | 2 ± 1 |
| DU4475 | 2990 ± 30 | 8 ± 3 | 332 ± 18 | 10 ± 3 |
| Nontransformed | | | | |
| MCF12A | 75 ± 20 | 15 ± 5 | 12 ± 4 | 5 ± 2 |
| Hs578Bst | 65 ± 5 | 18 ± 3 | 26 ± 6 | 4 ± 2 |

In vitro translation was performed with PPT-I-containing poly A RNA in the presence or absence of cytosolic extracts from mammary epithelial cells. Aliquots, 2 l, were TCA-precipitated and then determined for SP-IR by ELISA. The data is represented as protein levels/g poly A. Details of the technique are described in above. For SP-IR, each point is the mean (+SD) of six different experiments. For IL1α, IL6 andSCF, each point is the mean (±SD) of three different experiments. Each experiment was performed with poly A RNA isolated from bone marrow stroma from a different donor and cell extracts from a different cell passage.

To further confirm that Substance P is present in the translation reactions, we performed imnmunoreactive techniques. We used equivalent quantities of proteins to immunoprecipitate Substance P. Immune complexes were analyzed in western blots to determine whether the precipitates were consistent with the predicted size of Substance P. In reactions without cytosolic extract, a light band was developed Cytosolic extracts from breast cancer cells showed strong bands. In contrast, no band was visible in reactions performed with extracts from normal mammary epithelial cells, MCF12A.

We next determined if the putative translational factors in the cytoplasm of breast cancer cells were unique to PPT-I mRNA. We studied the translation rate for IL-1α, IL-6 and SCF. For SCF, we used poly A RNA from IL-1α-stimulated stroma because this cytokine is expected to induce SCF. For IL-1α and IL-6, we isolated poly A RNA from SCF stimulated stroma. Immune complexes, analyzed in western blots showed no band for IL-1α and SCF. However, translation was increased for IL-6. ELISA was utilized to quantitate these results (Table 3). The results described in this section show that cytosolic extracts from breast cancer cells increase SP-IR and IL-6 in an in vitro translation system. No effect was observed for SCF and IL-1α.

Example 4

Role of PPT-I Peptides in the Proliferation of Breast Cancer Cells

Increased expression of PPT-I and NK-1 in breast cancer cells (Tables 1 and 2) led to the next set of experiments. A functional role for these genes in breast cancer is established by determining whether PPT-I peptides, endogenously produced by breast cancer cells, can induce their proliferation through autocrine and/or paracrine mechanisms. This question was addressed in six different experiments using clonogenic assay. Dose-response and timecourse studies indicated that the optimal parameters are 1 nM antagonist and two wk of incubation. Assays performed with various concentrations of cells showed distinct differences among various treatments if the cultures were performed with $10^3$ cells/ml. NK-1 or NK-2 antagonists blunted breast cancer cell proliferation by approximately 40% when compared to cultures with media alone (Table 4). As seen in Table 4, cells cultured with both antagonists blunted cell proliferation by 20%. There was no significant difference (p>0.5) in cell proliferation when normal mammary epithelial cells (MCF12A and H5578Bst) were cultured with the antagonists. The data indicate that alone, NK-1 and NK-2 antagonists blunted the proliferation of breast cancer cell lines and together, they exert more potent inhibitory effects. Reduced colony formation was not due to necrosis since >99% of the cells were trypan blue negative in suspension cultures, performed for two weeks with antagonists.

TABLE 4

Effects of NK Receptor antagonists on the proliferation of breast cancer cell line

| Cell lines | Media | CP96,345 # of colonies/$10^3$ cells (±SD) | SR48968 | CP96,345 + SR 48968 |
|---|---|---|---|---|
| Transformed | | | | |
| T47D (20%) | 150 ± 5 | 60 ± 4 (40%) | 65 ± 7 (43%) | 30 ± 3 |
| BT474 (190) | 180 ± 10 | 70 ± 5 (39%) | 65 ± 8 (36%) | 34 ± 6 |
| ZR7530 (21%) | 165 ± 5 | 68 ± 8 (41%) | 60 ± 10 (36%) | 35 ± 5 |
| MDAMB-330 (22%) | 170 ± 8 | 65 ± 5 (38%) | 64 ± 4 (38%) | 38 ± 8 |
| Du4475 (19%) | 160 ± 8 | 63 ± 6 (39%) | 60 ± 5 (38%) | 30 ± 6 |
| NonTransformed | | | | |
| MCF12A 104%) | 210 ± 12 | 198 ± 18 (94%) | 200 ± 9 (95%) | 220 ± 13 |
| Hs578Bst 103%) | 200 ± 11 | 201 ± 12 (1%) | 210 ± 11 (105%) | 205 ± 15 |

Cells, $10^3$, were cultured for 2 weeks in methyl cellulose matrix with 1 mM of CP 96,345, SR48968 or both antagonists. After two weeks, colonies were consisting of greater than 10 cells were counted. The results are expressed as the mean of four differeint experiments (+SD). Each experimental time point is the average of duplicate cultures. The percentage of cells cultured in media alone is shown in parentheses.

Example 5

Sequences of the Human PPT-I, NK-2 and SP-R Promoters, and the PPT-I 3' End.

The entire sequence of human PPT-I promoter has been cloned and is set forth herein as SEQ ID NO:1. Cloning and analysis of this promoter are described in the examples below. The sequences of the NK-2 and SP-R promoters are set forth as SEQ ID NOS: 2, and 3. As mentioned previously, each of these promoter sequences can be operably linked to reporter genes to assess agents which influence expression of PPT-I, NK-2 and SP-R. Accordingly, one aspect of the invention encompasses methods to assess such agents.

```
                                                            SEQ ID NO:1
-740  CTATAGGGCA CGCGTGGTCG ACGGCCCGGC TGGTAAATTC CCCTTTCTCC -691

-690  AAAATGTAAA ATAAATCTGC TTCCATCTTC TAAAATACTA TGGGACTAAA -641

-640  CATCCTTTTG TTATGCTAAG GAAAAGCCAG TATTCGCGTT GATTTAGAAG -591

-590  AGGGATGTTC TGGTTATAGA ACGATGCTGT GTCTCAGAAA CACTTAAATA -541

-540  CTATTAAGCT AGAAATAGAA GGGAAAATAA TGCTTCCCCG CATCTCCCCT -491

-490  CAAGTGTAGT CCTCTTTTTT TAGCCTGATT TCCGACGAAA TGTCTGAATG -441

-440  CCTACAGTTA TTTGGCCATC CTGAAAAGTG CAACTTATCC TGACGTCTCG -391

-390  AGGGACGGAA AAGTTACCGA AGTCCAAGGA ATGAGTCACT TTGCTCAAAT -341

-340  TTGATGAGTA ATATCAGGTG TCATGAAACC CAGTTTCGAA GGAGAGGGGA -291

-290  GGGGGCGTCA GATCTGCAGA CGGAAGCAGG CCGCTCCGGA TTGGATGGCG -241

-240  AGACCTCGAT TTTCCTAAAA TTGCGTCATT TAGAACCCAA TTGGGTCCAG -191

-190  ATGTTATCGG CATCGACGAG TTACCGTCTC GGAAACTCTC AATCACGCAA -141

-140  GCGAAAGGAG AGGAGGCGGC TAATTAAATA TTGAGCAGAA AGTCGCGTGG -91

-90  GGAGAATGTC ACGTGGGTCT GGAGGCTCAA GGAGGCTGGG ATAAATACCG -41

-40  CAAGGCACTG AGCAGGCGAA AGAGCGCGCT CGGACCTCCT TTCCCGGCGG -10
      Exon 1.

+11  CAGCTACCGA GAGTGCGGAG CGACCAGCGT GCGCTCGGAG AACCAGAGAA +60

+61  CTCAGCACCC CGCGGGACTG TCCGTCGCAG TAAGTGCCCG CGCGGTGCTG +90

Intron 1
 +91  GCCGCGGCTG CCCGGGTCAT CCCACCCCGC ATCTGTCCGA GGTGGCCGCG +140

+141  CTGGGGGCGC CGCTGCGGCG AGGGACAGTG GGGAGACTGG CTTCCCAAAC +190

+191  GCCAACGCCC CTCTTTGTCT TCCACCTGCA GAGTTTCCTG GTTTGAAGGT +240

+241  GTGGGTTGGT GGGTTAGGGG GCTGGGGGAG CTGGGATTCA GGGAGAAGAG +290

+291  GGTTGGAGAA TCTTTGGGAC GCGATTCTCT CGCCTAACCG GTACAGGTGA +340

+341  GACTTCAGTC CTTATGTTTT TGATCTTGGT TCATCCGTTG TGGGGCAGAA +390

+391  AATTCTGTTG CTTTAACTCT TGGATAACCA CCCCTAATAG ATACATTATT +440

+441  TCTCTCTTTG GTGTCTTCTC CTCCTACCCC TTCCCAGAAA TCCGACATGA +490
      Exon 2

+491  AAATCCTCGT GGCCTTGGCA TCTTTTTTTC TGACGG
```

SEQ ID NO: 2: Upstream sequences and exon 1 of the NK-2 receptor. The TATA box is at bases 369-376. Genbank Accession No. M75101.

5' Untranslated region—Upstream of Exon I, NK-2

```
  1  CGACGGCCCT GGCTGGTACT GCTACTGTTG CCGCCACCAA CAGAGATCAA

51  AGGCAGAGAC CCTTCTGCTA GGGTCCAAAG TCCAAACAGG CCACTCCAGA

101  GAGGAAACAG GCACACAGGC ACACACCCAC GGGAGGAGTA GGGGCCCAGG
```

-continued

```
 151 AAGCACTCCC TCCCCAAGGG CAAGGATGGG GTTCCCATTC CACCCAGCAC

201 ATGCTCCTCA CATCTGCACA GCAGGGAGAC CAAACAATAG ATACAATTTC

251 AGTGCCTGAT TGTCGATCAA CTTACCCAGA AGTTCATAAT CCGAAAAATC

301 CATAAACAAG CTCTTTCAAT TTCAGCATGT TTAAGTTTCA TGACTTATGG

351 TTTAGTGTTG TTTTTATATT GGATTCCATG GGTGGCATAA TCTTTTCAGC

401 ACTAGAGACC TTTAAAGGTC TTTCTCAGCT CACCCCGGGA GACAAGGGCT

451 GGGTGTCAGG AAAGTGACAC ACAGGGAGAA GCAGAAAATG GACTGGGAGT

501 GTGGGGCCG AGGCCCAGCC ACGAGAAACC CAGGCGGTGC AAGGCAGAGC

551 CCTGGGAGCA CAGAGGCTGC TGTGCCGTGG GTTGCTGGTG AATGAGAAGC

601 CTCCTCTGCT TTAATGAAGA ACATGCCCCC CCCGACTCCC GCTAATCCTG

651 CCCTGCCTTC ATGATCCACA CACCACAGGT GTGCACACGT TCATGCGTGT

701 GTGTGAGCTT AACACGTCAG CCGCACATAC AGTTGCACAG AAACATCTTC

751 ACTGCTTTCA CACACGTGCA CACAGTCAAA TGACCAGGAG CAGGATCTTG

801 GGGCAAACCT AGAGCAGCTT CTCAGGAGTT AGAACTCCAG CTTTGCTGTG

851 GTTCCCAGAA GAGCCCTGAC TTTGTCCTAA GACAGTGGTT CTCAAAGTGA

901 AGTGCTGGCT CCAGCAGCAT CAGTATCACC TGGGAACTCG CTGGAAACGC

951 TCCGGGTTCT GGCTTCTCCT CCTAGAGCGC CCAGAGCTGT GGGGTCCTCC

1001 CTTCGGGCCA GAAACTCCAA TCATAAGTTT CTATGTACCA ACCCCTGTGC

1051 TAAGTAGACT TTGTGCACAT TATCTCCATT TAAAATTTCA CAAATGTACT

1101 GTCAGATGCA CACCCATTTT TCTATACTTC TACAGATGGG GTAAGACAGA

1151 GCTCAGAAAG GTTAAGAGAC TTGCCTGGAG TCACCAAACC AGGCTCCAAC

1201 TCCTTCTGTA TTCAGAATCA CTCTTCAGAC GTAGCTCCTG TCCTGGGCTG

1251 AAAGTCAACA TCCGCCGAGA GCTGGGCCCT CTGTACCAGC CCCATCTCCC

1301 CCAAGTCTCT CCCTGCCTCT GCAGCCAGTC CTAAATCTTT CAAGAGACAA

1351 GGCCAAGCAG GGGGTGGGAC CAGGGGCGGG AGCCAAAGCC CCCCCTCGTG

1401 AGCAGGCAGC ACCTCTGCCA AGGCCCCCAC TGGCCCTGCC CCAGAGAACG

1451 GCAGGGAAGC TGCAGCGAGG GCTGGCAGCT GGCAGAGTCC TGAGCACCCA

1501 GCACCCAGCC CGGCTTGCAG CCCAAAGCCT GGAGAGAGGC TGCTGCGCCA

1551 TTGACCTGTG GACTCCAGAG ACTCCCGCTG TGCATTCCTC TGATCTGGAA

1601 GGTTTCCTGA ATTACGTGAC GAGAAACCTG GGTTCGAGTC CTAACTTGTC

1651 ACCAACGTTC CTGAGTGACC TGGGCTGGTC CCGTCCCCTT GGAATCTCTG

1701 TCTTCCATCT CTTCAGCGAA GGGGTTGATT TATAAGGGTG TTTTCTGCTC
                                        TATA signal
1751 TGACACTGTG ATTTGAATTC TGTGTTTCCA CATGATATTC GAGAAGTCTG

1801 GCCGGAAGGA TGGAATCTGA AATCACAATG GTTCTGGACT GGGCTTTGTG

1851 CTCAGCCCAG CTCATCTTTG CCTGAGACCT AGGAGTGGCC CCAGGCTCTC

1901 CTGATGTGCC ACCACGCTTG GCATCTGCTC CTCTCCCTGC CCCCATATTC
```

-continued
```
1951 CCATGCTCTG AAGGGGAGTT CTCTTTCATA GCAAATCCGA GAGGAGCCGA

2001 GGAGCCAGGT CCTTTGTTCC AGACCCAGAA GCAGCCATGG GGACCTGTGA

Exon 1
2051 CATTGTGACT GAAGCCAATA TCTCATCTGG CCCTGAGAGC AACACCACGG

2101 GCACCACAGC CTTCTCCATG CCCAGCTGGC AACTGGCACT GTGGGCCACA

2151 GCCTACCTGG CCCTGGTGCT GGTGGCCGTG ACGGGTAATG CCATCGTCAT

2201 CTGGATCATC CTGGCCCATC GGAGGATGCG CACAGTCACC AACTACTTCA

2251 TCGTCAATCT GGCGCTGGCT GACCTCTGCA TGGCTGCCTT CAATGCCGCC

2301 TTCAACTTTG TCTATGCCAG CCACAACATC TGGTACTTTG GCCGTGCCTT

2351 CTGCTACTTC CAGAACCTCT TCCCCATCAC AGCCATGTTT GTCAGCATCT

2401 ACTCCATGAC CGCCATTGCT GCCGACAG
```

20

SEQ ID NO: 3: Gene for Substance P receptor. Genbank Accession No: X65177. The TATA box is at bases 1339-1342.

```
   1 ggatccaatt tttgcccggc ataagtgtat agtaaatttc ccagccttaa agcacttccc 61 gagagatgct ttgagcgctc gcggtaccag tgcgtaaacg ccgctccccg gctggcgcgg 121 gtgtgcgcca actccaacct gcgcgcaagt ctgccggtgc gcgctccagt cccacagctc 181 cgagtccccg cagtgaaagg aggggcggt gcaccggggt agatgggccc ctgaggactc 241 ccggggttca gttttccgcg gctgccaaga gggccaagtt ggacagtggc agggtcctga 301 agcagatcag caacaaccgc aagtgctcca gcccaggtc ctcagacacg gaggaaaacg 361 acaagaggcg gacacacaac gtcttggaac gtcagaggag aacgagctg aagcgcagct 421 ttttgccct gcgtgaccag atccctgaat tggaaaacaa cgaaaaggcc cccaaggtag 481 tgatcctcaa aaaagccacc gcctacatcc tgtccattca agcagacgag cacaagctca 541 cctctgaaaa ggacttattg aggaaacgac gagaacagtt gaaacacaaa ctcgaacagc 601 ttcgaaactc tggtgcataa actgacctaa ctcgaggagg agctggaatc tctcgtgaga 661 gtaaggagaa cggttccttc tgacagaact gatgcgctgg aattaaaatg catgctcaaa 721 gcctaacctc acaaccttgg ctggggcttt gggactgtaa gcttagagac tgtcacttcc 781 caggtgaatc agctagccag gtaactgagc tagatatttt gtggggtgt ttcctaaaca 841 cagcctcagg aaagttgttt tcgggacacc tggaccaggg agtcgtcgcc tctggcttct 901 cggtagctgg agcgcggccc ggagcgcggc gctggcacat cgcccccaca catgaccgtt 961 tcccattgcc acaggcaagc cgcctctgca gagctgtctc agggctctgg gcttcattcc 1021 ctggaagttg attgtcctcc actccagctg tttcccaaat ccttccttcc tcccagcacc 1081 cctcgtgcaa cgacgattcc agctgcggac cgcatctgtg tcagttactt ccaagccacc 1141 tactgccccc tcgcggagtg cgtggggctc ccggctcgca gactcccacg gcaagtagca 1201 agcagcaaaa ggcgtggtag ctgcggcggt ggaatgagac agttgtcaac agctggcgca 1261 cgtgccgccg tgcgcaccgg gactggcgag tacgcagccc aggtactgcc ccttcccagt 1321 gacgtctctg caggggtta taaaagcctc gtgcgcagct aactcgcgag ctgagcaacc 1381 cgaaccgaga ggtgcccgcg aaactgcagg cggcggcagc ggcagcaaaa gagaaggaaa 1441 aatctccagc tggatacgaa gctccagaat cctggccata ggctcagaac ttttacaggt
```

```
-continued
1501 cgcgctgcaa tgggccccca cttcgctcct aagtcctcac gcagcacagg gctttgcctt 1561 tccctgcgga ggaaggagaa ataggagttg caggcagcag caggtgcata aatgcggggg 1621 atctcttgct tcctagaact gtgaccggtg gaatttcttt ccctttttca gtttaccgca 1681 agagagatgc tgtctccaga cttctgaact caaacgtctc ctgaagcttg aaagtggagg 1741 aattcagagc caccgcgggc aggcgggcag tgcatccaga agcgtttata ttctgagcgc 1801 cagttcagct ttcaaaaaga gtgctgccca gaaaaagcct tccaccctcc tgtctggctt 1861 tagaaggacc ctgagcccca ggcgccagcc acaggactct gctgcagagg ggggttgtgt 1921 acagatagta gggctttacc gcctagcttc gaaatggata acgtcctccc ggtggactca 1981 gacctctccc caaacatctc cactaacacc tcggaaccca atcagttcgt gcaaccagcc 2041 tggcaaattg tcctttgggc agctgcctac acggtcattg tggtgacctc tgtggtgggc 2101 aacgtggtag tgatgtggat catcttagcc cacaaaagaa tgaggacagt gacgaactat 2161 tttctggtga acctggcctt cgcggaggcc tccatggctg cattcaatac agtggtgaac 2221 ttcacctatg ctgtccacaa cgaatggtac tacggcctgt tctactgcaa gttccacaac 2281 ttcttcccca tcgccgctgt cttcgccagt atctactcca tgacggctgt ggcctttgat 2341 aggtgagatt agcctttgtg aaaaggcgag aaagtgctca tagaggacca tggcattgct 2401 gtgaggtttg gaactgggtg gggtatgggt caagtggaag attggccact ctgagggttt 2461 ttttactgat ca
```

The 3' end of the PPT-I gene is set forth herein as SEQ ID NO: 4. This sequence includes the mRNA encoding $^2$-PPT-I.

```
   1 gagagtgcgg agcgaccacg tgcgctcgga ggaaccagag aaactcagca ccccgcggga 61 ctgtccgtcg caaaatccaa catgaaaatc ctcgtggcct tggcagtctt ttttcttgtc 121 tccactcagc tgtttgcaga agaaatagga gccaatgatg atctgaatta ctggtccgac 181 tggtacgaca gcgaccagat caaggaggaa ctgccggagc cctttgagca tcttctgcag 241 agaatcgccc ggagacccaa gcctcagcag ttctttggat taatgggcaa acgggatgct 301 gattcctcaa ttgaaaaaca agtggccctg ttaaaggctc tttatggaca tggccagatc 361 tctcacaaaa gacataaaac agattccttt gttggactaa tgggcaaaag agctttaaat 421 tctgtggctt atgaaaggag tgcaatgcag aattatgaaa gaagacgtta ataaactacc 481 taacattatt tattcagctt catttgtgtc aatgggcaat gacaggtaaa ttaagacatg 541 cactatgagg aataattatt tatttaataa caattgttta gggttgaaaa ttcaaaaagt 601 gtttatttt catattgtgc caatatgtat tgtaaacatg tgtttaatt ccaatatgat 661 gactccctta aaatagaaat aagtggttat ttctcaacaa agcacagtgt taaatgaaat 721 tgtaaaacct gtcaatgata cagtccctaa agaaaaaaaa tcattgcttt gaagcagttg 781 tgtcagctac tgcggaaaag gaaggaaact cctgacagtc ttgtgctttt cctatttgtt 841 ttcatggtga aaatgtactg agattttggt attacactgt atttgtatct ctgaagcatg 901 tttcatgttt tgtgactata tagagatgtt tttaaaagtt tcaatgtgat tctaatgtct 961 tcatttcatt gtatgatgtg ttgtgatagc taacatttta aataaaagaa aaaatatctt 1021 g
```

SEQ ID NO:14 is a variant of SEQ ID NO:1.

```
   1 cgacggcccg gctggtaaat tcccctttct ccaaaatgta aaataaatct gcttccatct
  61 tctaaaatac tatgggacta aacatccttt tgttatgcta aggaaaagcc agtattcgcg
 121 ttgatttaga agagggatgt tctggttata aacgatgct gtgtctcaga aacacttaaa
 181 tactattaag ctagaaatag aagggaaaat aatgcttccc cgcatctccc ctcaagtgta
 241 gtcctctttt tttagcctga tttccgacga aatgtctgaa tgcctacagt tatttggcca
 301 tcctgaaaag tgcaacttat cctgacgtct cgagggacgg aaaagttacc gaagtccaag
 361 gaatgagtca ctttgctcaa atttgatgag taatatcagg tgtcatgaaa cccagtttcg
 421 aaggagaggg gagggggcgt cagatctgca gacggaagca ggccgctccg gattggatgg
 481 cgagacctcg attttcctaa aattgcgtca tttagaaccc aattgggtcc agatgttatg
 541 ggcatcgacg agttaccgtc tcggaaactc tcaatcacgc aagcgaaaqg agaggaggcg
 601 gctaattaaa tattgagcag aaagtcgcgt ggggagaatg tcacgtgggt ctggaggctc
 661 aaggaggctg ggataaatac cgcaaggcac tgagcaggcg aaagagcgcg ctcggacctc
 721 ctttcccggc ggcagctacc gagagtgcgg agcgaccagc gtgcgctcgg agaaccagag
 781 aactcagcac cccgcgggac tgtccgtcgc agtaagtgcc cgcgcggtgc tggccgcggc
 841 tgcccgggtc atcccacccc gcatctgtcc gaggtggccg cgctggggc gccgctgcgg
 901 cgagggacag tggggagact ggcttcccaa acgccaacgc ccctctttgt cttccacctg
 961 cagagtttcc tggtttgaag gtgtgggttg gtgggttagg gggctggggg agctgggatt
1021 cagggagaag agggttggag aatctttggg acgcgattct ctcgcctaac cggtacaggt
1081 gagacttcag tccttatgtt tttgatcttg gttcatccgt tgtggggcag aaaattctgt
1141 tgctttaact cttggataac caccctaat agatacatta tttctctctt tggtgtcttc
1201 tcctcctacc ccttcccaga aatccgac
```

SEQ ID NO: 15 is the PPT-I cDNA (Genbank NM 013998)

```
   1 gcgccgcaag gcactgagca ggcgaaagag cgcgctcgga cctccttccc ggcggcagct
  61 accgagagtg cggagcgacc agcgtgcgct cggaggaacc agagaaactc agcaccccgc
 121 gggactgtcc gtcgcaaaat ccaacatgaa aatcctcgtg gccttggcag tcttttttct
 181 tgtctccact cagctgtttg cagaagaaat aggagccaat gatgatctga attactggtc
 241 cgactggtac gacagcgacc agatcaagga ggaactgccg gagccctttg agcatcttct
 301 gcagagaatc gcccggagac ccaagcctca gcagttcttt ggattaatgg caaacggga
 361 tgctggacat ggccagatct ctcacaaaat ggcttatgaa aggagtgcaa tgcagaatta
 421 tgaaagaaga cgttaataaa ctacctaaca ttatttattc agcttcattt gtgtcaatgg
 481 gcaatgacag gtaaattaag acatgcacta tgaggaataa ttatttattt aataacaatt
 541 gtttggggtt gaaaattcaa aaagtgttta tttttcatat tgtgccaata tgtattgtaa
 601 acatgtgttt taattccaat atgatgactc ccttaaaata gaataagtg gttatttctc
 661 aacaaagcac agtgttaaat gaaattgtaa aacctgtcaa tgatacagtc cctaaagaaa
 721 aaaaatcatt gctttgaagc agttgtgtca gctactgcgg aaaaggaagg aaactcctga
 781 cagtcttgtg cttttcctat ttgttttcat ggtgaaaatg tactgagatt ttggtattac
 841 actgtatttg tatctctgaa gcatgtttca tgttttgtga ctatatagag atgttttaa
```

```
-continued
901 aagtttcaat gtgattctaa tgtcttcatt tcattgtatg atgtgttgtg atagctaaca 961 ttttaaataa aagaaaaaat atcttgaaaa aaaaaaaaaa aaa
```

Example 6

Cloning of PPT-I Promoter

The human β-PPT-I sequence was used as a guide in nested PCR to clone upstream relative to Exon 2. PCR was performed with templates from five human genomic libraries (PromoterFinder DNA Walking Kit, Clontech). Outer (AP1) and inner (AP2) adapter sequences linked to the 5' ends and gene specific primers, +124/+151 and +88/+116 (Harmar, A. J. et al., supra) were used in nested PCR. Procedures were performed according to manufacturer's instructions. Single bands from three libraries were cloned into pNoTA/T7 (5 Prime→3 Prime, Boulder, Colo.). The resulting DNA product was sequenced using techniques well known in the art. The sequenced DNA indicated overlapping sequences. The cloned fragment was analyzed using Wisconsin Package, Version 10 Genetics Computer Group, Inc., Madison, Wis.

PCR was used to sub-clone the sense and anti-sense orientations of PPT-I-p1.2 and the following fragments in pGL3-basic: 1. −722 bp relative to Exon 1, Upstream/N0, 2. Upstream/N1, −722Δ−589, 3. Exon 1, 4. Intron 1 and, 5. Exon1/Intron 1. To obtain the desired orientation, PCR primers were synthesized with sequences for Hind III and Kpn I in the desired location.

Example 7

Identification of PPT-I Promoter

By genomic walk using nested PCR with primers specific for Exon-2 of β-PPT-I cDNA, three overlapping sequences were isolated from different DNA libraries, upstream of Exon 2, PPT-I. FIG. 2 shows the sequence of the longest fragment (1.225 kb, PPT-I-p 1.2). This sequence overlaps with Exon 1 of the cloned sequence of β-PPT-I (Harmar, A. J. et al., supra This information was used together with computer-assisted analyses to determine the location of the TAATA box. PPT-I-p1.2 consists of the following: Exon 2 (+499, ATG and downstream sequences omitted), Intron 1 (+89/+498), Exon 1 (+1/+89) and −722 nt relative to Exon 1, hereafter referred as "Upstream/N0".

To determine if PPT-I-p1.2 contains promoter activity, we ligated the sense and anti-sense sequences in the reporter (luciferase) vector, pGL3-basic, and then quantitated reporter activity in transfected, primary human bone marrow stromal cells. These cell types were chosen to study PPT-I-p1.2 because they could be induced to express endogenous PPT-I (Kramer, M. S. et al. 1998, Science 281:1640) and would therefore contain necessary trans-acting factors to study PPT-I promoter. A second advantage of using stromal cells is that this strategy could examine the regulation of PPT-I in bone marrow stroma, the hematopoietic supporting cells (Mullersieburg, C. E. et al. 1995. Stem Cells 13:477), thus providing insights into the role of this gene in hematopoiesis.

We first determined if the primary stromal cells could incorporate the transfected DNA. In situ hybridization for ampicillin vector showed that >80% of the stromal cells incorporated plasmid DNA. Co-labeling by immunofluorescence with specific antibodies indicated that most of the plasmid DNA was taken up by two of the three major stromal subsets: macrophage and fibroblast. Cells transfected with PPT-I-p1.2 in the sense orientation resulted in 480±30 increase in normalized luciferase activity (FIG. 3) and <0.8 fold in the anti-sense orientation (not shown). These results indicate that PPT-I-p1.2 contains promoter activity. In addition to bone marrow stromal cells, we also observed promoter activity in two other types of cells, CCL64 and skin fibroblasts.

Figure 3:
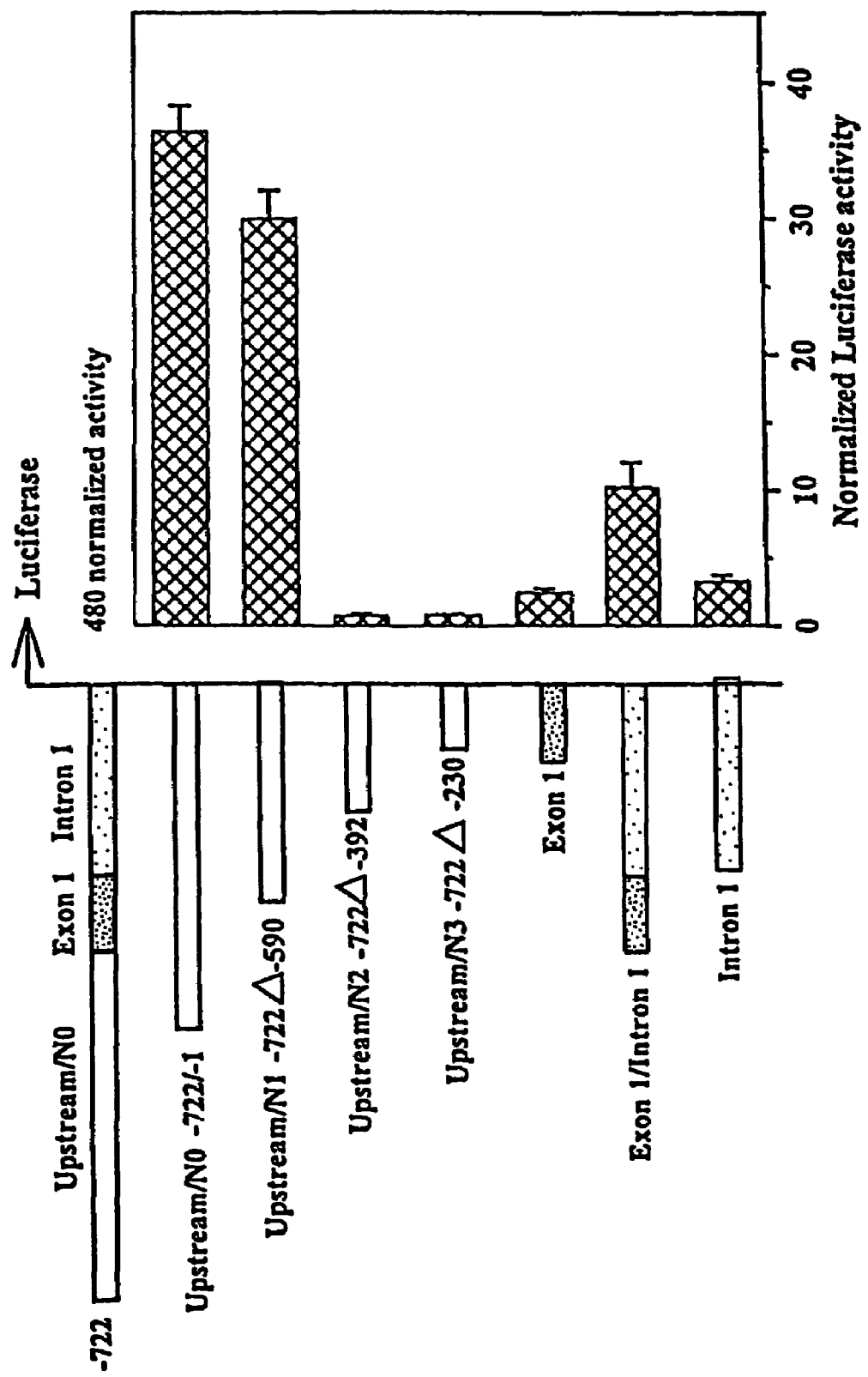
FIG. 3 shows Luciferase activities by PPT-I-p1.2 fragments in bone marrow stroma. Different fragments of PPT-I-p1.2 were ligated in pGL3, upstream of the luciferase gene and then transfected in bone marrow stroma. The results are the mean (±SD) of 7 experiments; each performed with a different bone marrow donor.

We next narrowed the region containing promoter activity by sub-cloning different fragments of PPT-I-p1.2 in the sense and anti-sense orientations in pGL3-basic. FIG. 3 shows the ratio of luciferase/β-gal in stroma transfected with Upstream/N0, Upstream/N1 (−722Δ−589), Upstream/N2 (−722Δ−392), Upstream/N3 (−722Δ−230), Exon 1, Exon 1/Intron 1 or Intron 1. There was no significant difference in luciferase activities in cells that were transfected with Upstream/N0 (36±2) and Upstream/N1 (30±2), p>0.5. Further deletion in the 5' region (Upstream/N2 and Upstream/N3) resulted in <2 normalized luciferase activity. Therefore, the 5' end of Upstream/N0 contains of sequences that are important for promoter activity. The relative lack of promoter activity by Exon 1 and Intron 1 further supports the presence of a promoter in Upstream/N0 (FIG. 3). In contrast to the individual sequences, Exon 1, placed in tandem with Intron 1, showed significant increase in luciferase activity, suggesting that these sequences contain a second, but weak promoter and/or regions that might be stabilizing the DNA. Taken as a whole, the results shown in FIG. 3 indicate that PPT-I-p1.2 has a strong (Upstream/N0) and possibly a weak (Exon 1/Intron 1) promoter. Regulatory regions in Exon 1/Intron 1 are interesting because the protein-coding region for each of the four PPT-I transcripts is within Exon 2 (Harmar, A. J. et al., supra).

Example 8

Characterization of CRE and CRE-like in Upstream/N0

Computer analyses of Upstream/N0 indicated consensus sequences for two CRE that we termed CRE and CRE-like (FIG. 2). We first established if these two sequences could bind CRE-binding proteins using ICERIIγ in gel shift assay (Molina, C. A. et al, 1993. Cell 75:875), FIG. 4A. The results indicated that ICERIIγ binds to wild type CRE and CRE-like indicating that the latter could be a CRE site (Table 5). However, ICERIIγ did not bind to the mutants (FIG. 4A) indicating that the particular mutation adequately prevents interaction with the specific proteins. These results justify the use of mutants in studies to determine the specificity of CRE and CRE-like in the analyses of PPT-I promoter.

TABLE 5

Wild type and mutant cAMP response elements (CRE and CRE-like).

| Gene | Sequence | Homology |
|---|---|---|
| CRE-somatostatin | 5'-TGACGTCT | |
| CRE-PPT-I (wild type) | 5'-TGACGTCT | CREB, CRE |

TABLE 5-continued

Wild type and mutant cAMP response elements (CRE and CRE-like).

| Gene | Sequence | Homology |
|---|---|---|
| CRE-PPT-I (mutant) | 5'-<u>AGA</u>T<u>GTTT</u> | |
| CRE-like-PPT-I | 5'-TTGCGTCA | CREB, CRE, ATF |
| CRE-like-PPT-I (mutant) | 5'-TTG<u>T</u>G<u>CAC</u> | |

Italics and underlined sequences represent points of mutations.

Since the experimental model included transfection of bone marrow stroma to study CRE and CRE-like, we next determined if these cells express CRE-binding proteins and whether they could be phosphorylated by FK, a cAMP-inducing agent. Consistent with other cell types, the levels of CREM did not show any significant change regardless of cell stimulation (FIG. 4B: lanes 1-3, top arrow). However, stromal cell stimulation with FK resulted in the presence of ICER after 2 h and an increase by 5 h (FIG. 4B, lanes 2 and 3, lower arrow). ICER was not detected in unstimulated cells (FIG. 4B, lane 1, lower arrow). FIG. 4C showed constitutive expression of CREB proteins. FK stimulation resulted in phosphorylation of CRE-binding proteins (CREB, CREM and ATF): CREB and CREM co-migrated together, (FIG. 4D, top bands, lanes 2 and 3) and ATF-1, lower bands (FIG. 4D, lanes 2 and 3). The results shown in FIGS. 4B to 4D showed that similar to cells from several sources, bone marrow stroma expresses CRE-binding proteins.

Figure 5B:
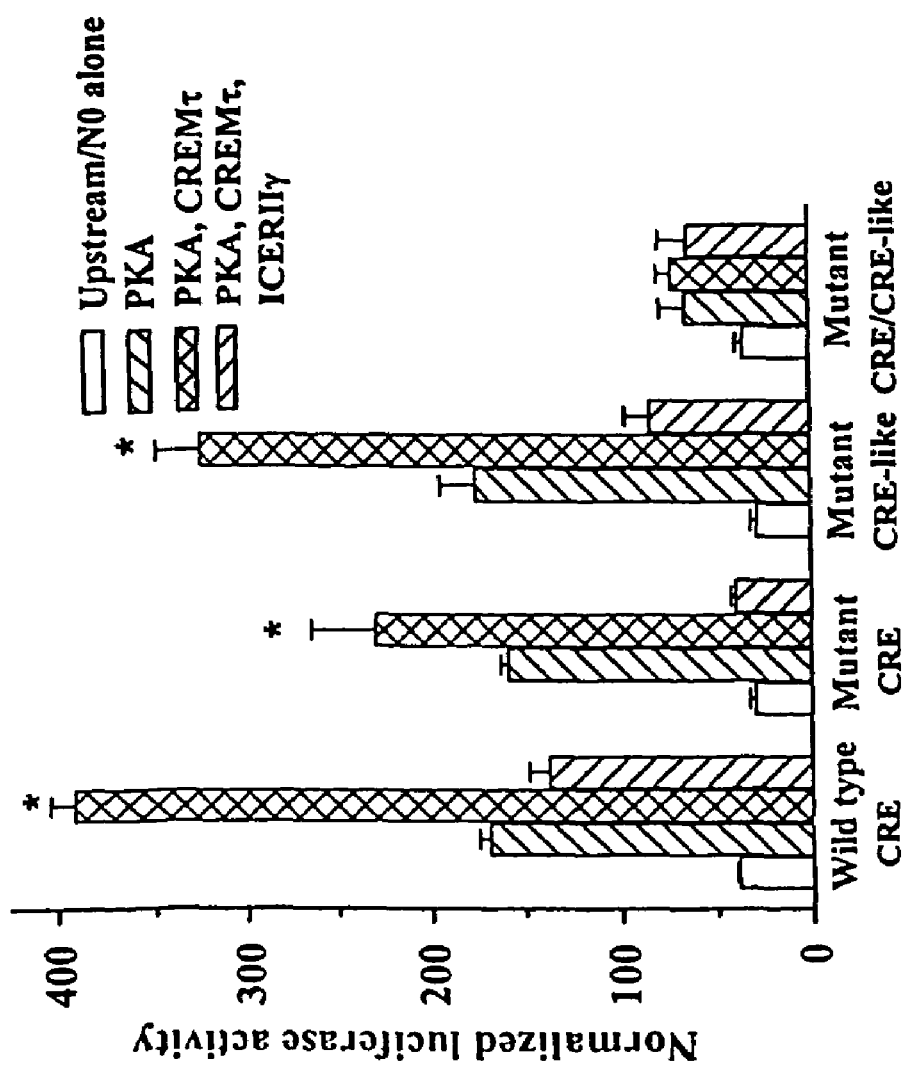
FIG. 5B: Reporter activity was determined 48 h after transfection in cell lysates. *p<0.05 vs. Upstream/N0 or PKA, CREMτ, ICERIIγ.
Figure 5A:
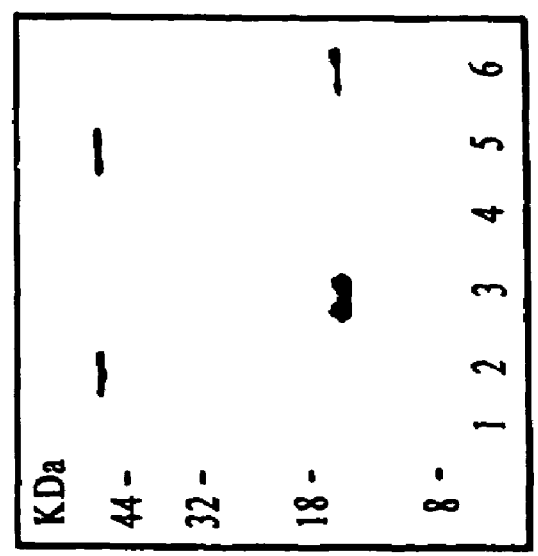
FIG. 5A: Western blots with rabbit antibodies verified that the transfected CREMτ and ICERIIγ were expressed in the co-transfected cells, representative figure shows; Lanes 1: no transfection, 2 and 5: CREMτ, 3 and 6: ICERIIγ and 4: salmon sperm DNA.

Before addressing the importance of CRE and/or CRE-like in the induction of PPT-I by cytokines, we determined if these sequences are important for PPT-I promoter activity using two different approaches. In the first approach, we co-transfected bone marrow stroma with pGL3-Upstream/N0 and/or the transcription factors that interact with CRE: CREMτ (activator) or ICERIIγ (repressor). Because activation of CREM requires PKA phosphorylation (Molina, C., supra), we included PKA-expression vectors. Cells were transfected with PKA+CREMτ, PKA or PKA+CREMτ+ICERIIγ, and the levels of luciferase activities were quantitated. In the second approach, CRE and/or CRE-like was mutated in Upstream/N0 and then co-transfected. Western analysis confirmed the expression of CREMτ and ICERIIγ in the transfected stromal cells (FIG. 5A). The results of both approaches are shown in FIG. 5B. Co-transfection of pGL3-Upstream/N0 with wild type or mutant CRE showed no change in luciferase activity (open bars). This demonstrated that sequences other than CRE and CRE-like are involved in baseline promoter activity. Co-transfection with PKA showed no change in luciferase activity in the wild type or single mutant. Since PKA phosphorylates proteins other than those that bind to CRE sites, the data shown for co-transfection with PKA and single mutants indicated that either one CRE site could mediate optimal luciferase activity or that non-CRE sites are involved in activation of the PPT-I promoter. There was significant reduction of luciferase activity (p<0.05) when PKA was co-transfected with CRE double mutant. This suggests that although other sites might be involved in the activation of PPT-I promoter, an available CRE site is required for optimum activity given the appropriate activation signal. The specificity of CRE-mediated responses is shown by the significantly reduced activity of luciferase (p<0.01) when ICERIIγ was co-transfected with PKA and CREMτ. Comparing luciferase activity in the co-transfectants of the double mutants with wild type CRE and CRE-like indicated that in the presence of the appropriate transcription factors, both CRE sites could contribute in either a synergistic or additive manner with other transcription factors to induce Upstream/N0. However, CRE and CRE-like binding factors demonstrated synergistic rather than additive effects.

Example 9

Role of CRE and CRE-like in PPT-I Induction: Model by IL-1α and SCF

Cytokines are important inducers of PPT-I (Ramewshwar, P. 1997, supra). We used two representative cytokines (IL-1 and SCF) to determine the physiologic significance for CRE and CRE-like in PPT-I regulation. These two cytokines were used because they induce PPT-I and the high affinity receptor for PPT-I peptides, neurokinin-1 (NK-1R) in bone marrow stroma, and they also activate the cAMP pathway. Table 6 shows the validity for using IL-1α and SCF in this model. Compared to unstimulated cells, IL-1α and SCF stimulation resulted in significant increase of endogenous PPT-I mRNA (p<0.005) and also modulate the mRNA for the receptors, NK-1 and NK-2 (Table 6). These observations are consistent with the modulation of NK-1 and NK-2 in bone marrow cells to regulate hematopoiesis (Rameshwar, P. 1997, supra; Rameshwar, P. et al. 1997, supra; Culman, J. et al. 1995, Canadian J. Pharmacol. 73, 885-891).

TABLE 6

βPPT-I and NK-2 mRNA levels in SCF and IL-α-stimulated BM stroma

| | Molecules/μg total RNA | | |
|---|---|---|---|
| Stimuli | β-PPT-I | NK-1 | NK-2 |
| Unstimulated | 16 ± 5 | <10 | 2609 ± 70 |
| SCF | 1336 ± 134* | 5253 ± 170* | 273 ± 19* |
| IL-1a | 4849 ± 121* | 8106 ± 91* | 968 ± 26* |

Confluent BM stroma was stimulated with 8 ng/ml SCF or 2.5 ng/ml IL-1a for 16 h in serum-free α-MEM. Quantitative RT-PCR determined steady-state mRNA.
*p < 0.05 vs. unstimulated, n = 10.

Figure 6B:
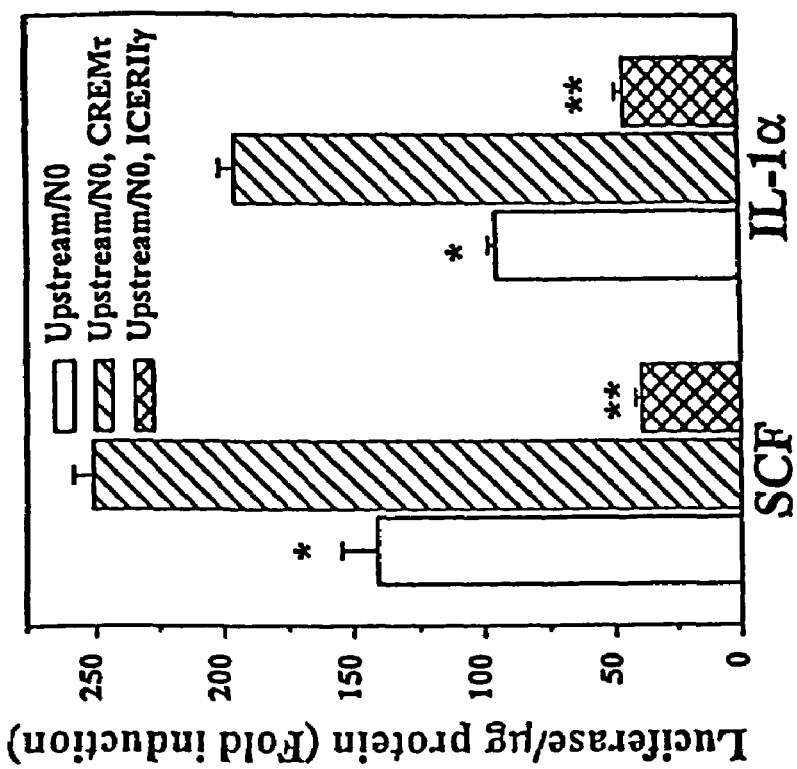
FIG. 6 shows the effects of CRE and CRE-like in the induction of Upstream/N0. Bone marrow stroma was transfected with pGL3-Upstream/N0 containing wild type CRE, mutant CRE, mutant CRE-like or double mutant (CRE and CRE-like) and then stimulated with optimal SCF or IL-1α (FIG. 6A). In parallel studies, stroma was co-transfected with Upstream/N0 containing wild type CRE and CRE-like and, CREMτ or ICERIIγ. Stroma was stimulated 24 h after transfection with optimal SCF or IL-1α, Table 2 (FIG. 6B). After 10 h luciferase activity was determined in cell lysates. Stimulation time was deduced from time-course studies ranging from 2 to 48 h.
FIG. 6A: **p<0.05 vs. unstimulated stroma, *p<0.05 vs. wild type CRE.
Figure 6A:
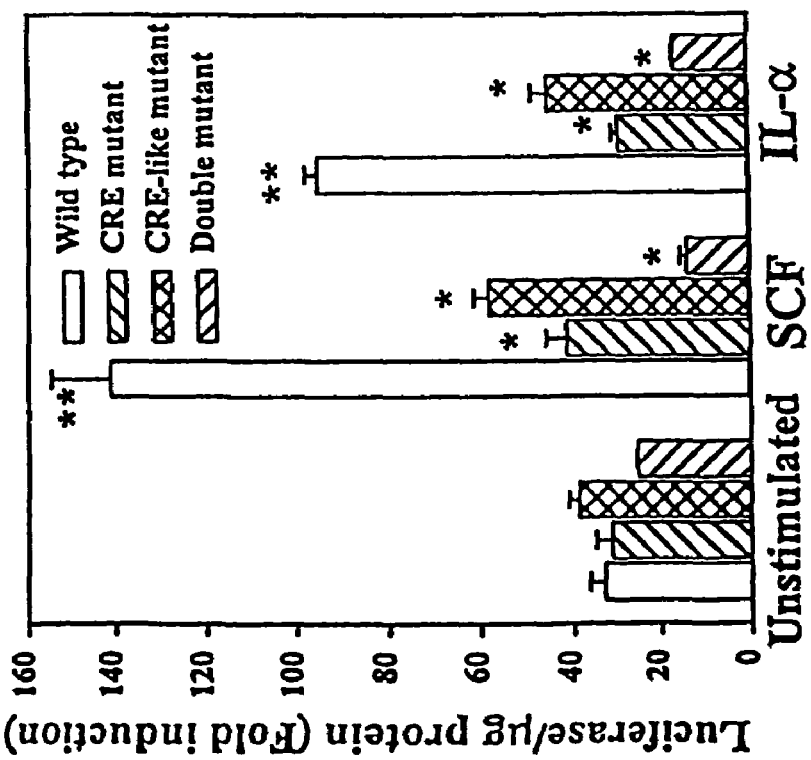

To address if SCF and IL-1a required CRE and CRE-like for PPT-I induction, we transfected bone marrow stroma with pGL3-Upstream/N0 with wild type or mutant CRE and/or CRE-like and then stimulated the transfectants with SCF or IL-1a. Compared to unstimulated cells, SCF and IL-1a stimulation showed 4- and 3-fold increase in luciferase activities respectively (FIG. 6A). SCF and IL-1a showed no significant induction of luciferase in cells transfected with the double mutants (FIG. 6A). However, there was 1.5 fold less luciferase activity in the double mutants compared to cells transfected with wild type or single mutant (FIG. 6A). These observations demonstrates that both CRE and CRE-like have roles in the activation of Upstream/N0. Furthermore, the data suggest that with respect to PPT-I induction, the CRE sites are be the dominant regulatory regions for inducers that are associated with stimulation of the cAMP pathway and in the absence of CRE-binding proteins, cytokine could be repressors of PPT-I induction.

Generally, biological functions do not occur in a microenvironment with only one stimulus. Therefore, we designed the next set of experiments with the aim of obtaining insights into the role of the two CRE in a microenvironment that is has have multiple soluble factors that are associated with the activation of cAMP pathway, such as cytokines and neurotrophic factors. Because CREM is activated by many cytokines, this protein was overexpressed as a model to mimic the presence of other stimuli that could activate CRE-binding proteins. Stroma was co-transfected with pGL3-Upstream/N0 and CREMτ and then stimulated with IL-1α or SCF. For both cytokines, co-transfection with CREMτ resulted in significant induction of luciferase compared to cells transfected with pGL3-Upstream/N0 alone (FIG. 6B). Luciferase induction by both cytokines was significantly reduced by co-transfection with ICERIIγ (FIG. 6B). These results supported an important role for CRE in PPT-I induction by at least two PPT-I-inducible cytokines that are associated with stimulation of cAMP pathway.

Example 10

Autocrine Activation of PPT-I through SCF-mediated Expression of NK-1

In the next set of experiments, we investigated the possibility for an indirect mechanism in the activation of PPT-I promoter. We hypothesize that this pathway could occur independently, or in addition to other pathways through concomitant induction of endogenous PPT-I and the high affinity receptor (NK-1) for its peptides by the same stimulus e.g. cytokine (Table 6). The production of PPT-I peptides could interact with the G-protein coupled NK-1 to activate cAMP pathway (Vaupel, R. et al. 1998, *Endocrinology* 123, 2140-2145), consequently regulating PPT-I expression through CRE and CRE-like. We first induced NK-1 with optimal SCF for 36 h ($5052 \pm 50$ molecules/μg total RNA). Since SCF induces endogenous PPT-I (Table 6), we used ELISA (Singh, D. et al, supra) to quantitate the level of its major translation product, immunoreactive-SP (SP-IR), in stroma cell extracts. The results are presented as the total levels of SP-IR in 1 ml of cell extract, obtained from one confluent stromal layer, grown in 25 cm$^2$ tissue culture flask. The results showed $115 \pm 8$ pg/ml (n=5, $\pm$SD) of SP-IR after 36 h in SCF-stimulated stromal extracts whereas, extracts from unstimulated stroma consisted <1 pg/ml. We therefore asked whether SCF-mediated production of SP could stimulate the cells through autocrine mechanism. To address this, we incubated the SCF-stimulated cells with 10 nM of an NK-1-specific antagonist (CP-99,994) and then quantitated luciferase activity. To ensure that the manipulation by the transfection did not blunt the production of endogenous Substance P, we determined Substance P levels in five different experiments in which stroma was stimulated with SCF. SP-IR at time 0 and 4 h post-transfection were $110 \pm 18$ and $122 \pm 14$ pg/ml, $\pm$SD respectively. Despite the high levels of SP-IR, luciferase activity was significantly reduced in the presence of the antagonist (FIG. 7A). Antagonist alone did not affect luciferase activity compared to transfectants with vector alone. The results of these experiments show that NK-1 is at least partly required for the activation of PPT-I promoter by SCF.

We next determined if SCF could be initiating a response so that PPT-I is able to auto regulate its own expression. To address this, we stimulated bone marrow stroma with 1 nM of the major PPT-I peptide, substance P, SP (Sigma), and then determined the levels of PPT-I mRNA by quantitative RT-PCR. Compared to undetectable PPT-I mRNA in unstimulated cells, cultures with SP showed significant increase in β-PPT-I, p<0.01 (Table 7). NK-1-specific antagonist (CP-99,994) did not completely blunt the effects of SP since at 10 nM, there was only 7-fold reduction (Table 7). The data showed that SP, at least partly through NK-1 could mediate its own expression. Similarly, induction of endogenous PPT-I by SCF is blunted by CP-99,994 (Table 7). In summary, the results in this section used two different approaches, transient transfection and induction of endogenous PPT-I, to show that SCF could induce PPT-I directly and/or indirectly through activation of the G-protein-coupled NK-1 (FIG. 7B).

TABLE 7

Induction of PPT-I by substance P (SP)

| Stimuli | β-PPT-I (molecules/μg total RNA) |
|---|---|
| Unstimulated or CP-99,994 | <1 |
| SP | 284 ± 12* |
| SP + CP-99,994 | 42 ± 4 |
| SCF | 1324 ± 76** |
| SCF + CP-99,994 | 119 ± 8 |

BM stroma were stimulated with 1 nM SP, 8 ng/ml SCF and/or 10 nM CP-99,994 for 16 h. After this, βPPT-I levels were quantitated using total RNA. *p < 0.01 vs. SP + CP-99,994, n = 6, ±SD; **p < 0.01 vs. SCF + CP-99,994. The results are shown with optimum concentration of CP-99, 994, derived from dose-response studies. The levels of NK-1 mRNA in stroma stimulated with SCF in the presence or absence of CP-99,994 were 49,195 ± 110 and 5,085 ± 140 molecules/μg total RNA respectively.

Example 11

Cell-specific Activity of PPT-I Promoter

Figure 8:
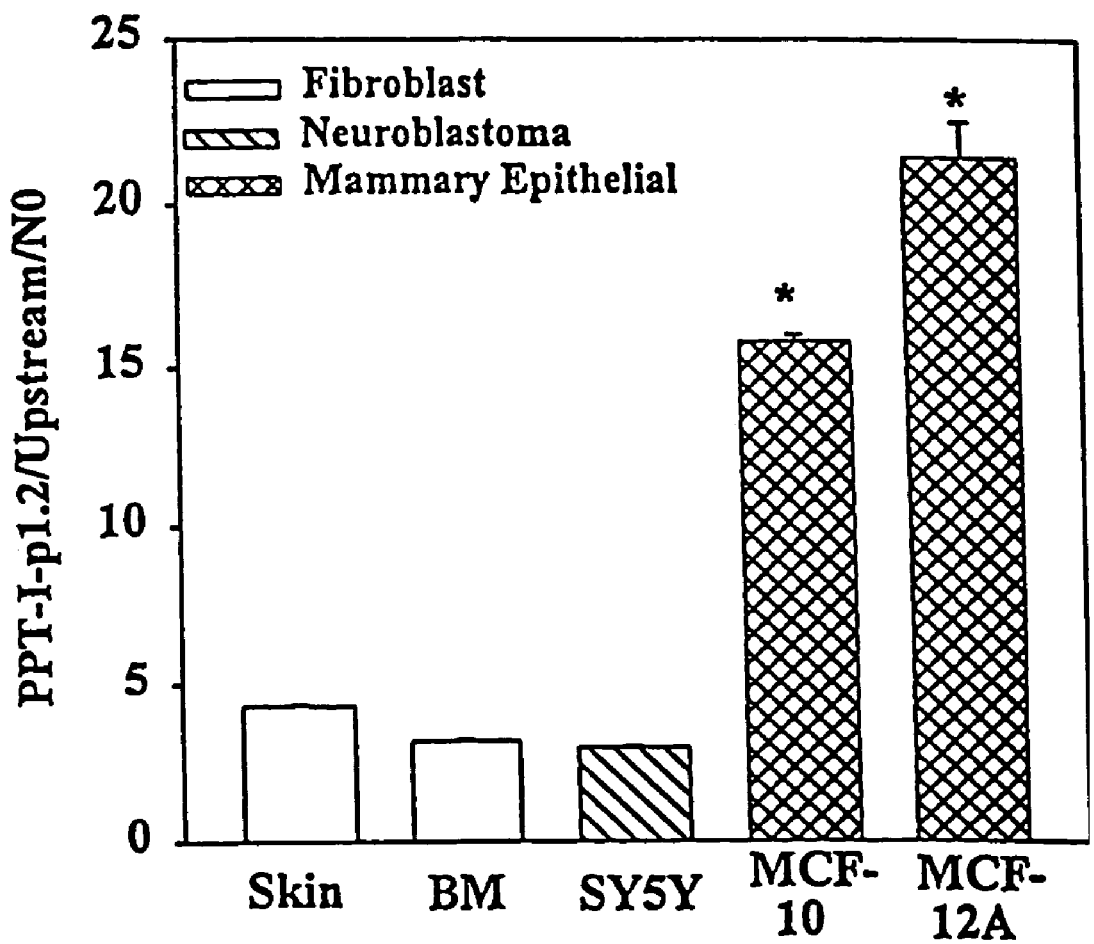
FIG. 8 depicts fibroblasts (CRL 1502) or 5× passaged primary bone marrow adherent cells and normal mammary epithelial cells, MCF-10 and MCF-12A were transfected with pGL3-PPT-I-p1.2 or pGL3-Upstream/N0. The techniques for luciferase activity and normalization with β-gal are described in FIG. 3. The results are represented as the ratio of luciferase induction in cells transfected with PPT-I-p1.2 over Upstream/N0. *p<0.05 vs. fibroblast or SY5Y, n=7, ±SD.

PPT-I is expressed with different efficiency and by different stimuli in particular tissues (Rameshwar P. 1997, supra; Hennig, I., supra; Hart, R. P., supra). In bone marrow stromal cells, although macrophage and fibroblasts express endogenous PPT-I when stimulated by IL-1α, the levels in macrophage are relatively higher than fibroblasts. Similar differences are observed in IL-1α-stimulated bone marrow and skin fibroblasts. The data described for FIG. 7B indicate that NK-1 expression regulates PPT-I expression through signaling of cAMP. Since the expression of NK-1 is different in bone marrow stroma, inducible, (Ramewshwar, P. 1997, supra) and neural cells, constitutive (Rameshwar, P. et al 1997, supra), we determined if there is tissue and/or cell specificity in its regulation. We chose relevant cells based on the role of PPT-I in areas of major clinical interests such as breast cancer, hematological disorders and brain-associated injuries and/or dysfunctions. Thus, we used fibroblasts from bone marrow and skin, undifferentiated neuroblastoma (SY5Y) and mammary epithelial cells. Since Intron 1 and Exon 1 could have regulatory regions (FIG. 3), we used PPT-I-p1.2 and Upstream/N0 for cell transfection. Because transfection efficiency could vary depending on the cell source, for comparison purposes, cells were co-transfected with pβ-gal and each transfection normalized with β-gal activity. The results, summarized in FIG. 8 indicate that mammary epithelial cells transfected with pGL3-PPT-I-p1.2 showed significant increase in luciferase compared to fibroblasts and SY5Y. There was no difference in reporter activity in the two sources of fibroblasts. We also observed comparable luciferase activities in transfected fibroblasts and SY5Y.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

We claim:

1. An isolated nucleic acid molecule comprising SEQ ID NO:1 or SEQ ID NO:14.

2. An expression vector comprising the nucleic acid molecule of claim 1, operably linked to a heterologous gene that encodes a gene product.

3. An isolated host cell transformed with the vector of claim 2.

* * * * *

SEQUENCE LISTING

<160> NUMBER OF SEQ ID NOS: 15

<210> SEQ ID NO 1
<211> LENGTH: 1286
<212> TYPE: DNA
<213> ORGANISM: Homo sapiens

<400> SEQUENCE: 1

| | | | | | |
|---|---|---|---|---|---|
| ctatagggca | cgcgtggtcg | acggcccggc | tggtaaattc | cccttttctcc | aaaatgtaaa | 60 |
| ataaatctgc | ttccatcttc | taaaatacta | tgggactaaa | catccttttg | ttatgctaag | 120 |
| gaaaagccag | tattcgcgtt | gatttagaag | agggatgttc | tggttataga | acgatgctgt | 180 |
| gtctcagaaa | cacttaaata | ctattaagct | agaaatagaa | gggaaaataa | tgcttccccg | 240 |
| catctcccct | caagtgtagt | cctctttttt | tagcctgatt | tccgacgaaa | tgtctgaatg | 300 |
| cctacagtta | tttggccatc | ctgaaaagtg | caacttatcc | tgacgtctcg | agggacggaa | 360 |
| aagttaccga | agtccaagga | atgagtcact | ttgctcaaat | ttgatgagta | atatcaggtg | 420 |
| tcatgaaacc | cagtttcgaa | ggagagggga | ggggcgtca | gatctgcaga | cggaagcagg | 480 |
| ccgctccgga | ttggatggcg | agacctcgat | tttcctaaaa | ttgcgtcatt | tagaacccaa | 540 |
| ttgggtccag | atgttatggg | catcgacgag | ttaccgtctc | ggaaactctc | aatcacgcaa | 600 |
| gcgaaaggag | aggaggcggc | taattaaata | ttgagcagaa | agtcgcgtgg | ggagaatgtc | 660 |
| acgtgggtct | ggaggctcaa | ggaggctggg | ataaataccg | caaggcactg | agcaggcgaa | 720 |
| agagcgcgct | cggacctcct | ttcccggcgg | cagctaccga | gagtgcggag | cgaccagcgt | 780 |
| gcgctcggag | aaccagagaa | ctcagcaccc | cgcgggactg | tccgtcgcag | taagtgcccg | 840 |
| cgcggtgctg | gccgcggctg | cccgggtcat | cccacccccgc | atctgtccga | ggtggccgcg | 900 |
| ctgggggcgc | cgctgcggcg | agggacagtg | gggagactgg | cttcccaaac | gccaacgccc | 960 |
| ctctttgtct | tccacctgca | gagtttcctg | gtttgaaggt | gtgggttggt | gggttagggg | 1020 |
| gctggggggag | ctgggattca | gggagaagag | ggttggagaa | tctttgggac | gcgattctct | 1080 |
| cgcctaaccg | gtacaggtga | gacttcagtc | cttatgtttt | tgatcttggt | tcatccgttg | 1140 |
| tggggcagaa | aattctgttg | ctttaactct | tggataacca | ccctaatag | atacattatt | 1200 |
| tctctctttg | gtgtcttctc | ctcctacccc | ttcccagaaa | tccgacatga | aaatcctcgt | 1260 |
| ggccttggca | tcttttttttc | tgacgg | | | | 1286 |

<210> SEQ ID NO 2
<211> LENGTH: 2428
<212> TYPE: DNA
<213> ORGANISM: Homo sapiens

<400> SEQUENCE: 2

| | | | | | |
|---|---|---|---|---|---|
| cgacggccct | ggctggtact | gctactgttg | ccgccaccaa | cagagatcaa | aggcagagac | 60 |
| ccttctgcta | gggtccaaag | tccaaacagg | ccactccaga | gaggaaacag | gcacacaggc | 120 |
| acacacccac | gggaggagta | ggggcccagg | aagcactccc | tccccaaggg | caaggatggg | 180 |
| gttcccattc | cacccagcac | atgctcctca | catctgcaca | gcagggagac | caaacaatag | 240 |
| atacaatttc | agtgcctgat | tgtcgatcaa | cttaccaga | agttcataat | ccgaaaaatc | 300 |
| cataaagaag | ctcttttcaat | ttcagcatgt | ttaagtttca | tgacttatgg | tttagtgttg | 360 |
| ttttatatt | ggattccatg | ggtggcataa | tctttttcagc | actagagacc | tttaaaggtc | 420 |
| tttctcagct | caccccggga | gacaagggct | gggtgtcagg | aaagtgacac | acagggagaa | 480 |

-continued

```
gcagaaaatg gactgggagt gtggggccg aggcccagcc acgagaaacc caggcggtgc      540
aaggcagagc cctgggagca cagaggctgc tgtgccgtgg gttgctggtg aatgagaagc      600
ctcctctgct ttaatgaaga acatgccccc cccgactccc gctaatcctg ccctgccttc      660
atgatccaca caccacaggt gtgcacaggt tcatgcgtgt gtgtgagctt aacacgtcag      720
ccgcacatac agttgcacag aaacatcttc actgctttca cacacgtgca cacagtcaaa      780
tgaccaggag caggatcttg gggcaaacct agagcagctt tcaggagtt agaactccag       840 ctttgctgtg gttcccagaa gagccctgac tttgtcctaa gacagtggtt ctcaaagtga      900
agtgctggct ccagcagcat cagtataccc tgggaactcg ctggaaacgc tccgggttct      960
ggcttctcct cctagagcgc ccagagctgt ggggtcctcc cttcgggcca gaaactccaa     1020
tcataagttt ctatgtacca cccctgtgc taagtagact ttgtgcacat tatctccatt      1080
taaaatttca caaatgtact gtcagatgca cacccatttt tctatacttc tacagatggg     1140
gtaagacaga gctcagaaag gttaagagac ttgcctggag tcaccaaacc aggctccaac     1200
tccttctgta ttcagaatca ctcttcagac gtagctcctg tcctgggctg aaagtcaaca     1260
tccgccgaga gctgggccct ctgtaccagc cccatctccc ccaagtctct ccctgcctct     1320
gcagccagtc ctaaatcttt caagagacaa ggccaagcag ggggtgggac caggggcggg     1380
agccaaagcc cccctcgtg agcaggcagc acctctgcca aggcccccac tggccctgcc      1440
ccagagaacg gcagggaagc tgcagcgagg gctggcagct ggcagagtcc tgagcaccca     1500
gcacccagcc cggcttgcag cccaaagcct ggagagaggc tgctgcgcca ttgacctgtg     1560
gactccagag actcccgctg tgcattcctc tgatctggaa ggtttcctga attacgtgac     1620
gagaaacctg ggttcgagtc ctaacttgtc accaacgttc ctgagtgacc tgggctggtc     1680 ccgtccccctt ggaatctctg tcttccatct cttcagcgaa ggggttgatt tataagggtg    1740
ttttctgctc tgacactgtg atttgaattc tgtgtttcca catgatattc gagaagtctg     1800
gccggaagga tggaatctga aatgacaatg gttctggact gggctttgtg ctcagcccag     1860
ctcatctttg cctgagacct aggagtggcc ccaggctctc ctgatgtgcc accacgcttg     1920
gcatctgctc ctctccctgc ccccatattc ccatgctctg aaggggagtt ctctttcata     1980
gcaaatccga gaggagccga ggagccaggt cctttgttcc agacccagaa gcagccatgg     2040
ggacctgtga cattgtgact gaagccaata tctcatctgg ccctgagagc aacaccacgg     2100
gcaccacagc cttctccatg cccagctggc aactggcact gtgggccaca gcctacctgg     2160
ccctggtgct ggtggccgtg acgggtaatg ccatcgtcat ctggatcatc ctggcccatc     2220
ggaggatgcg cacagtcacc aactacttca tcgtcaatct ggcgctggct gacctctgca     2280
tggctgcctt caatgccgcc ttcaactttg tctatgccag ccacaacatc tggtactttg     2340
gccgtgcctt ctgctacttc cagaacctct tccccatcac agccatgttt gtcagcatct     2400
actccatgac cgccattgct gccgacag                                        2428
```

<210> SEQ ID NO 3
<211> LENGTH: 2472
<212> TYPE: DNA
<213> ORGANISM: Homo sapiens

<400> SEQUENCE: 3

```
ggatccaatt tttgcccggc ataagtgtat agtaaatttc ccagccttaa agcacttccc       60
gagagatgct ttgagcgctc gcggtaccag tgcgtaaacg ccgctccccg gctggcgcgg      120
gtgtgcgcca actccaacct gcgcgcaagt ctgccggtgc gcgctccagt cccacagctc      180
```

```
cgagtcccg  cagtgaaagg  aggggggcggt  gcaccgggt   agatgggccc  ctgaggactc    240
ccggggttca  gttttccgcg  gctgccaaga  gggccaagtt  ggacagtggc  agggtcctga    300
agcagatcag  caacaaccgc  aagtgctcca  gccccaggtc  ctcagacacg  gaggaaaacg    360
acaagaggcg  gacacacaac  gtcttggaac  gtcagaggag  gaacgagctg  aagcgcagct    420 ttttgccct   gcgtgaccag  atccctgaat  tggaaaacaa  cgaaaaggcc  cccaaggtag    480
tgatcctcaa  aaaagccacc  gcctacatcc  tgtccattca  agcagacgag  cacaagctca    540
cctctgaaaa  ggacttattg  aggaaacgac  gagaacagtt  gaaacacaaa  ctcgaacagc    600
ttcgaaactc  tggtgcataa  actgacctaa  ctcgaggagg  agctggaatc  tctcgtgaga    660
gtaaggagaa  cggttccttc  tgacagaact  gatgcgctgg  aattaaaatg  catgctcaaa    720
gcctaacctc  acaaccttgg  ctggggcttt  gggactgtaa  gcttagagac  tgtcacttcc    780
caggtgaatc  agctagccag  gtaactgagc  tagatatttt  gtgggggtgt  ttcctaaaca    840
cagcctcagg  aaagttgttt  tcgggacacc  tggaccaggg  agtcgtcgcc  tctggcttct    900
cggtagctgg  agcgcggccc  ggagcgcggc  gctggcacat  cgcccccaca  catgaccgtt    960
tcccattgcc  acaggcaagc  cgcctctgca  gagctgtctc  agggctctgg  gcttcattcc   1020
ctggaagttg  attgtcctcc  actccagctg  tttcccaaat  ccttccttcc  tcccagcacc   1080
cctcgtgcaa  cgacgattcc  agctgcggac  cgcatctgtg  tcagttactt  ccaagccacc   1140
tactgccccc  tcgcggagtg  cgtggggctc  ccggctcgca  gactcccacg  gcaagtagca   1200
agcagcaaaa  ggcgtggtag  ctgcggcggt  ggaatgagac  agttgtcaac  agctggcgca   1260
cgtgccgccg  tgcgcaccgg  gactggcgag  tacgcagccc  aggtactgcc  ccttcccagt   1320
gacgtctctg  caggggggtta  taaaagcctc  gtgcgcagct  aactcgcgag  ctgagcaacc   1380
cgaaccgaga  ggtgcccgcg  aaactgcagg  cggcggcagc  ggcagcaaaa  gagaaggaaa   1440
aatctccagc  tggatacgaa  gctccagaat  cctggccata  ggctcagaac  ttttacaggt   1500
cgcgctgcaa  tgggccccca  cttcgctcct  aagtcctcac  gcagcacagg  gctttgcctt   1560
tccctgcgga  ggaaggagaa  ataggagttg  caggcagcag  caggtgcata  aatgcggggg   1620
atctcttgct  tcctagaact  gtgaccggtg  gaatttcttt  ccctttttca  gtttaccgca   1680
agagagatgc  tgtctccaga  cttctgaact  caaacgtctc  ctgaagcttg  aaagtggagg   1740
aattcagagc  caccgcgggc  aggcgggcag  tgcatccaga  agcgtttata  ttctgagcgc   1800
cagttcagct  ttcaaaaaga  gtgctgccca  gaaaaagcct  tccaccctcc  tgtctggctt   1860
tagaaggacc  ctgagcccca  ggcgccagcc  acaggactct  gctgcagagg  ggggttgtgt   1920
acagatagta  gggctttacc  gcctagcttc  gaaatggata  acgtcctccc  ggtggactca   1980
gacctctccc  caaacatctc  cactaacacc  tcggaaccca  atcagttcgt  gcaaccagcc   2040
tggcaaattg  tccttttgggc  agctgcctac  acggtcattg  tggtgacctc  tgtggtgggc   2100
aacgtggtag  tgatgtggat  catcttagcc  cacaaaagaa  tgaggacagt  gacgaactat   2160
tttctggtga  acctggcctt  cgcggaggcc  tccatggctg  cattcaatac  agtggtgaac   2220
ttcacctatg  ctgtccacaa  cgaatggtac  tacggcctgt  tctactgcaa  gttccacaac   2280
ttcttcccca  tcgccgctgt  cttcgccagt  atctactcca  tgacggctgt  ggcctttgat   2340
aggtgagatt  agcctttgtg  aaaaggcgag  aaagtgctca  tagaggacca  tggcattgct   2400
gtgaggtttg  gaactgggtg  gggtatgggt  caagtggaag  attggccact  ctgagggttt   2460
ttttactgat  ca                                                           2472
```

```
<210> SEQ ID NO 4
<211> LENGTH: 1021
<212> TYPE: DNA
<213> ORGANISM: Homo sapiens

<400> SEQUENCE: 4
gagagtgcgg agcgaccacg tgcgctcgga ggaaccagag aaactcagca ccccgcggga      60
ctgtccgtcg caaaatccaa catgaaaatc tcgtggcct tggcagtctt ttttcttgtc     120
tccactcagc tgtttgcaga agaaatagga gccaatgatg atctgaatta ctggtccgac    180
tggtacgaca cgaccagat caaggaggaa ctgccggagc cctttgagca tcttctgcag     240
agaatcgccc ggagacccaa gcctcagcag ttctttggat taatgggcaa acgggatgct    300
gattcctcaa ttgaaaaaca agtggccctg ttaaaggctc tttatggaca tggccagatc    360
tctcacaaaa gacataaaac agattccttt gttggactaa tgggcaaaag agctttaaat   420
tctgtggctt atgaaaggag tgcaatgcag aattatgaaa gaagacgtta ataaactacc    480
taacattatt tattcagctt catttgtgtc aatgggcaat gacaggtaaa ttaagacatg    540
cactatgagg aataattatt tatttaataa caattgttta gggttgaaaa ttcaaaaagt    600
gtttattttt catattgtgc caatatgtat tgtaaacatg tgtttttaatt ccaatatgat   660 gactccctta aaatagaaat aagtggttat ttctcaacaa agcacagtgt taaatgaaat    720
tgtaaaacct gtcaatgata cagtccctaa agaaaaaaaa tcattgcttt gaagcagttg    780
tgtcagctac tgcggaaaag gaaggaaact cctgacagtc ttgtgctttt cctatttgtt    840
ttcatggtga aaatgtactg agattttggt attacactgt atttgtatct ctgaagcatg    900
tttcatgttt tgtgactata tagagatgtt tttaaaagtt tcaatgtgat tctaatgtct    960
tcatttcatt gtatgatgtg ttgtgatagc taacatttta aataaaagaa aaatatcttg   1020
g                                                                   1021

<210> SEQ ID NO 5
<211> LENGTH: 25
<212> TYPE: DNA
<213> ORGANISM: Artificial Sequence
<220> FEATURE:
<223> OTHER INFORMATION: synthetic sequence

<400> SEQUENCE: 5
gtggagacaa gaaaaaagac tgcca                                            25

<210> SEQ ID NO 6
<211> LENGTH: 25
<212> TYPE: DNA
<213> ORGANISM: Artificial Sequence
<220> FEATURE:
<223> OTHER INFORMATION: synthetic sequence

<400> SEQUENCE: 6
gaagatgctc aaaggcgtcc ggcag                                            25

<210> SEQ ID NO 7
<211> LENGTH: 26
<212> TYPE: DNA
<213> ORGANISM: Artificial Sequence
<220> FEATURE:
<223> OTHER INFORMATION: synthetic sequence

<400> SEQUENCE: 7
ataattctgc attgcactcc tttcat                                           26
```

```
<210> SEQ ID NO 8
<211> LENGTH: 19
<212> TYPE: DNA
<213> ORGANISM: Artificial Sequence
<220> FEATURE:
<223> OTHER INFORMATION: synthetic sequence

<400> SEQUENCE: 8
aatttacctg tcattgccc                                                        19

<210> SEQ ID NO 9
<211> LENGTH: 18
<212> TYPE: DNA
<213> ORGANISM: Artificial Sequence
<220> FEATURE:
<223> OTHER INFORMATION: synthetic sequence

<400> SEQUENCE: 9
agcccttgga gcatcttc                                                         18

<210> SEQ ID NO 10
<211> LENGTH: 20
<212> TYPE: DNA
<213> ORGANISM: Artificial Sequence
<220> FEATURE:
<223> OTHER INFORMATION: synthetic sequence

<400> SEQUENCE: 10
agtctcctta ctgtgacacc                                                       20

<210> SEQ ID NO 11
<211> LENGTH: 20
<212> TYPE: DNA
<213> ORGANISM: Artificial Sequence
<220> FEATURE:
<223> OTHER INFORMATION: synthetic sequence

<400> SEQUENCE: 11
ctaccacctc tacttcatcc                                                       20

<210> SEQ ID NO 12
<211> LENGTH: 25
<212> TYPE: DNA
<213> ORGANISM: Artificial Sequence
<220> FEATURE:
<223> OTHER INFORMATION: synthetic sequence

<400> SEQUENCE: 12
ctgctggata aacttcttca ggtag                                                 25

<210> SEQ ID NO 13
<211> LENGTH: 25
<212> TYPE: DNA
<213> ORGANISM: Artificial Sequence
<220> FEATURE:
<223> OTHER INFORMATION: synthetic sequence

<400> SEQUENCE: 13
aggacagtga cgaactattt tctgg                                                 25

<210> SEQ ID NO 14
<211> LENGTH: 1228
<212> TYPE: DNA
<213> ORGANISM: Homo sapiens
```

<400> SEQUENCE: 14

```
cgacggcccg gctggtaaat tccccttct ccaaaatgta aaataaatct gcttccatct      60
tctaaaatac tatgggacta acatccttt tgttatgcta aggaaaagcc agtattcgcg     120
ttgatttaga agagggatgt tctggttata gaacgatgct gtgtctcaga aacacttaaa    180
tactattaag ctagaaatag aagggaaaat aatgcttccc cgcatctccc ctcaagtgta    240
gtcctctttt tttagcctga tttccgacga aatgtctgaa tgcctacagt tatttggcca    300
tcctgaaaag tgcaacttat cctgacgtct cgagggacgg aaaagttacc gaagtccaag    360
gaatgagtca ctttgctcaa atttgatgag taatatcagg tgtcatgaaa cccagtttcg    420
aaggagaggg gaggggggcgt cagatctgca gacggaagca ggccgctccg gattggatgg    480
cgagacctcg attttcctaa aattgcgtca tttagaaccc aattgggtcc agatgttatg    540
ggcatcgacg agttaccgtc tcggaaactc tcaatcacgc aagcgaaagg agaggaggcg    600
gctaattaaa tattgagcag aaagtcgcgt ggggagaatg tcacgtgggt ctggaggctc    660
aaggaggctg ggataaatac cgcaaggcac tgagcaggcg aaagagcgcg ctcggacctc    720
cttcccggc ggcagctacc gagagtgcgc agcgaccagc gtgcgctcgg agaaccagag     780
aactcagcac cccgcgggac tgtccgtcgc agtaagtgcc cgcgcggtgc tggccgcggc    840
tgcccgggtc atcccacccc gcatctgtcc gaggtggccg cgctggggc gccgctgcgg     900
cgagggacag tggggagact ggcttcccaa acgccaacgc ccctctttgt cttccacctg    960
cagagttcc tggtttgaag gtgtgggttg gtgggttagg gggctggggg agctgggatt    1020
cagggagaag agggttggag aatctttggg acgcgattct ctcgcctaac cggtacaggt   1080
gagacttcag tccttatgtt tttgatcttg gttcatccgt tgtggggcag aaaattctgt   1140
tgctttaact cttggataac caccctaat agatacatta tttctctctt tggtgtcttc   1200
tcctcctacc ccttcccaga aatccgac                                      1228
```

<210> SEQ ID NO 15
<211> LENGTH: 1003
<212> TYPE: DNA
<213> ORGANISM: Homo sapiens

<400> SEQUENCE: 15

```
gcgccgcaag gcactgagca ggcgaaagag cgcgctcgga cctccttccc ggcggcagct      60
accgagagtg cggagcgacc agcgtgcgct cggaggaacc agagaaactc agcaccccgc    120
gggactgtcc gtcgcaaaat ccaacatgaa atcctcgtg gccttggcag tcttttttct    180
tgtctccact cagctgtttg cagaagaaat aggagccaat gatgatctga attactggtc    240
cgactggtac gacagcgacc agatcaagga ggaactgccg gagcccttg agcatcttct    300
gcagagaatc gcccggagac ccaagcctca gcagttcttt ggattaatgg caaacggga    360
tgctggacat ggccagatct ctcacaaaat ggcttatgaa aggagtgcaa tgcagaatta    420
tgaaagaaga cgttaataaa ctacctaaca ttatttattc agcttcattt gtgtcaatgg    480
gcaatgacag gtaaattaag acatgcacta tgaggaataa ttatttattt aataacaatt    540
gtttggggtt gaaaattcaa aaagtgttta ttttcatat tgtgccaata tgtattgtaa     600
acatgtgttt taattccaat atgatgactc ccttaaaata gaataagtg gttatttctc     660
aacaaagcac agtgttaaat gaaattgtaa aacctgtcaa tgatacagtc cctaaagaaa    720
aaaaatcatt gctttgaagc agttgtgtca gctactgcgg aaaaggaagg aaactcctga    780
cagtcttgtg cttttcctat ttgttttcat ggtgaaaatg tactgagatt ttggtattac    840
```

```
                                              -continued
actgtatttg tatctctgaa gcatgtttca tgttttgtga ctatatagag atgtttttaa        900
aagtttcaat gtgattctaa tgtcttcatt tcattgtatg atgtgttgtg atagctaaca        960
ttttaaataa aagaaaaaat atcttgaaaa aaaaaaaaaa aaa                         1003
```